US007037493B2

(12) United States Patent
Goldman et al.

(10) Patent No.: US 7,037,493 B2
(45) Date of Patent: May 2, 2006

(54) METHOD OF INDUCING NEURONAL PRODUCTION IN THE BRAIN AND SPINAL CORD

(75) Inventors: Steven A. Goldman, South Salem, NY (US); Abdellatif Benraiss, Astoria, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/846,588

(22) Filed: May 1, 2001

(65) Prior Publication Data

US 2002/0049178 A1   Apr. 25, 2002

Related U.S. Application Data

(60) Provisional application No. 60/201,230, filed on May 1, 2000.

(51) Int. Cl.
*A61K 48/00* (2006.01)
*C12N 15/00* (2006.01)
*C12N 15/86* (2006.01)

(52) U.S. Cl. .................. 424/93.2; 435/320.1; 435/456
(58) Field of Classification Search .................. 514/44; 424/93.2; 435/320.1, 455, 456, 457, 377
See application file for complete search history.

(56) References Cited

U.S. PATENT DOCUMENTS

| | | | |
|---|---|---|---|
| 5,082,670 A | 1/1992 | Gage et al. | |
| 5,196,315 A | 3/1993 | Ronnett et al. | |
| 5,308,763 A | 5/1994 | Ronnett et al. | |
| 5,453,361 A * | 9/1995 | Yancopoulos et al. | 435/69.1 |
| 5,491,084 A | 2/1996 | Chalfie et al. | |
| 5,654,189 A | 8/1997 | Lee et al. | |
| 5,661,032 A | 8/1997 | Miller et al. | |
| 5,750,376 A | 5/1998 | Weiss et al. | |
| 5,753,505 A | 5/1998 | Luskin | |
| 5,753,506 A | 5/1998 | Johe | |
| 5,766,948 A | 6/1998 | Gage et al. | |
| 5,770,414 A | 6/1998 | Gage et al. | |
| 5,780,300 A | 7/1998 | Artavanis-Tsakonas et al. | |
| 5,830,858 A * | 11/1998 | Rosenthal et al. | 514/12 |
| 5,837,535 A | 11/1998 | Joseph et al. | |
| 5,851,832 A | 12/1998 | Weiss et al. | |
| 5,874,304 A | 2/1999 | Zolotukhin et al. | |
| 5,958,767 A | 9/1999 | Snyder et al. | |
| 5,965,440 A * | 10/1999 | Reeves | 424/93.21 |
| 5,968,829 A | 10/1999 | Carpenter | |
| 5,980,885 A | 11/1999 | Weiss et al. | |
| 6,000,772 A | 12/1999 | Miller et al. | |
| 6,071,889 A * | 6/2000 | Weiss et al. | 514/44 |
| 6,225,122 B1 | 5/2001 | Sah et al. | |
| 6,245,564 B1 | 6/2001 | Goldman et al. | |
| 2001/0024827 A1 | 9/2001 | Luskin | |

FOREIGN PATENT DOCUMENTS

| | | |
|---|---|---|
| WO | WO 94/02593 | 2/1994 |
| WO | WO 96/38541 | 5/1996 |
| WO | WO 97/07200 | 2/1997 |
| WO | WO 98/32879 | 7/1998 |
| WO | WO 99/29279 | 6/1999 |
| WO | WO 99/49014 | 9/1999 |
| WO | WO 00/23571 | 4/2000 |
| WO | WO 01/46384 A2 | 6/2001 |
| WO | WO 01/53503 A1 | 7/2001 |

OTHER PUBLICATIONS

Kirschenbaum et al., Brain-derived neurotrophic factor promotes the survival of neurons arising from the adult rat forebrain subependymal zone, 1995, Proc. Natl. Acad. Sci. USA, vol. 92, pp. 210-214.*
Ahmed et al., BDNF enhances the differentiation but not the survival of CNS stem cell-derived neuronal precursors, 1995, The Journal of Neuroscience, vol. 15, pp. 5765-5778.*
Shihabuddin et al., The search for neural progenitor cells: prospects for the therapy of neurodegenerative disease, 1999, Molecular Medicine Today, vol. 5, pp. 474-480.*
During et al., Towards gene therapy for the central nervous system, 1998, Molecular Medicine Today, pp. 485-493.*
Benraiss et al., In vivo transduction of the adult rat ventricular zone with an adenoviral BDNF vector increases neuronal production and recruitment to the olfactory bulb, 1999, Society for Neuroscience, vol. 25, p. 1028.*
Zigova et al., Intraventricular administration of BDNF increases the number of newly generated neurons in the adult olfactory bulb, 1998, Molecular and Cellular Neuroscience, vol. 11, pp. 234-245.*
Bajocchi et al., Direct in vivo gene transfer to ependymal cells in the central nervous system using recombinant adenovirus vectors, 1993, Nature Genetics, vol. 3, pp. 229-234.*
Jackowski, A. Neural injury repair: hope for the future as barriers to effective CNS regeneration become clearer. British Journal of Neurosurgery 9:303-317, 1995.*
Emerich, D.F. Neuroprotective possibilities for Huntington's disease. Exp. Opion. Biol. Ther. 1:467-479, 2001.*
Araujo et al. Glial cell line-derived neurotrophnic factor attenuates the excitoxin-induced behavioral and neurochemical deficits in a rodent model of Huntington's disease. Neuroscience 81:1099-1110, 1997.*
Anderson et al. Ciliary neurotrophic factor protects striatal output neurons in an animal model of Huntington disease. Proc. Natl. Acad. Sci. USA 93:7346-7351, 1996.*

(Continued)

*Primary Examiner*—Dave Trong Nguyen
*Assistant Examiner*—Quang Nguyen
(74) *Attorney, Agent, or Firm*—Nixon Peabody LLP

(57) ABSTRACT

The present invention relates to methods of inducing neuronal production in the brain, recruiting neurons to the brain, and treating a neurodegenerative condition by providing a nucleic acid construct encoding a neurotrophic factor, and injecting the nucleic acid construct intraventricularly into a subject's brain.

10 Claims, 22 Drawing Sheets

OTHER PUBLICATIONS

Frim et al. Effects of biologically delivered NGF, BDNF and bFGF on striatal excitotoxic lesions. Neuroreport 4:367-370, 1993 Abstract only.*

Gage et al., "Isolation, Characterization, and Use of Stem Cells From the CNS," *Annu. Rev. Neurosci.* 18:159-192 (1995).

Gage et al., "Survival and Differentiation of Adult Neuronal Progenitor Cells Transplanted to the Adult Brain," *Proc. Natl. Acad. Sci. USA* 92:11879-11883 (1995).

Gao et al., "Neurotrophin-4/5 (NT-4/5) and Brain-Derived Neurotrophic Factor (BDNF) Act at Later Stages of Cerebellar Granule Cell Differentiation," *J. Neurosci.* 15(4):2656-2667 (1995).

Memberg et al., "Proliferation, Differentiation, and Survival of Rat Sensory Neuron Precursors *In Vitro* Require Specific Trophic Factors," *Mol. Cell. Neurosci.* 6:323-335 (1995).

Hoshimaru et al., "Differentiation of the Immortalized Adult Neuronal Progenitor Cell Line HC2S2 into Neurons by Regulatable Suppression of the v-*myc* Oncogene," *Proc. Natl. Acad. Sci. USA* 93:1518-1523 (1996).

Ockel et al., "In Vivo Effects of Neurotrophin-3 During Sensory Neurogenesis," *Development* 122:301-307 (1996).

Gravel et al., "Adenoviral Gene Transfer of Ciliary Neurotrophic Factor and Brain-Derived Neurotrophic Factor Leads to Long-Term Survival of Axotomized Motor Neurons," *Nature Medicine* 3:765-770 (1997).

Ribotta et al., "Prevention of Motoneuron Death by Adenovirus-Mediated Neurotrophic Factors," *J. Neurosci. Res.* 48:281-285 (1997).

DiPolo et al., "Prolonged Delivery of Brain-Derived Neurotrophic Factor by Adenovirus-Infected Müller Cells Temporarily Rescues Injured Retinal Ganglion Cells," *Proc. Nat'l. Acad. Sci. USA* 95:3978-3983 (1998).

Fariñas et al., "Characterization of Neurotrophin and Trk Receptor Functions in Developing Sensory Ganglia: Direct NT-3 Activation of TrkB Neurons In Vivo," *Neuron* 21:325-334 (1998).

Fukumitsu et al., "Simultaneous Expression of Brain-Derived Neurotrophic Factor and Neurotrophin-3 in Cajal-Retzius, Subplate and Ventricular Progenitor Cells During Early Development Stages of the Rat Cerebral Cortex," *Neurosci.* 84(1):115-127 (1998).

Kempermann et al., "New Nerve Cells for the Adult Brain. Adult Neurogenesis and Stem Cell Concept in Neurological Research," *Nervenarzt* 69(10):851-857 (1998) (English abstract).

Isenmann et al., "Excess Target-Derived Brain-Derived Neurotrophic Factor Preserves the Transient Uncrossed Retinal Projection to the Superior Colliculus," *Mol. Cell. Neurosci.* 14:52-65 (1999).

Kukekov et al., "Multipotent Stem/Progenitor Cells with Similar Properties Arise from Two Neurogenic Regions of Adult Human Brain," *Experimental Neurology* 156:333-344 (1999).

Takahashi et al., "Retinoic Acid and Neurotrophins Collaborate to Regulate Neurogenesis in Adult-Derived Neural Stem Cell Cultures," *J. Neurobiology* 38:65-81 (1999).

Zaheer et al., "Enhanced Expression of Neurotrophic Factors by C6 Rat Glioma Cells After Transfection with Glia Maturation Factor," *Neuroscience Letters* 265:203-206 (1999).

Alvarez-Buylla et al., "Neuronal Stem Cells in the Brain of Adult Vertebrates," *Stem Cells* 13:263-72 (1995).

Craig et al., "In Vivo Growth Factor Expansion of Endogenous Subependymal Neural Precursor Cell Populations in the Adult Mouse Brain," *J. Neurosci.* 16(8):2649-2658 (1996).

Driesse et al., "Intra-CSF Administered Recombinant Adenovirus Causes an Immune Response-Mediated Toxicity," *Gene Therapy* 7:1401-1409 (2000).

Goldman et al., "Neuronal Precursors of the Adult Rat Subependymal Zone Persist into Senescence, With No Decline in Spatial Extent or Response to BDNF," *J. Neurobiology* 32:554-566 (1997).

Goldman et al., "Neural Precursors and Neuronal Production in the Adult Mammalian Forebrain," *Ann. N.Y. Acad. Sci.* 835:30-55 (1997).

Goldman et al., "Strategies Utilized by Migrating Neurons of the Postnatal Vertebrate Forebrain," *Trends in Neurosciences* 21(3):107-114 (1998).

Goldman et al., "*In Vitro* Neurogenesis by Neuronal Precursor Cells Derived from the Adult Songbird Brain," *J. Neurosci.* 12(7):2532-2541 (1992).

Gould et al., "Neurogenesis in the Neocortex of Adult Primates," *Science* 286:548-552 (1999).

Guan et al., "Selective Neuroprotective Effects with Insulin-Like Growth Factor-1 in Phenotypic Striatal Neurons Following Inschemic Brain Injury In Fetal Sheep," *Neuroscience* 95(3):831-839 (2000).

Ivkovic et al., "Expression of the Striatal DARPP-32/ARPP-21 Phenotype in GABAergic Neurons Requires Neurotrophins *In Vivo* and *In Vitro*," *J. Neurosci.* 19(13):5409-5419 (1999).

Kaplan, "Proliferation of Subependymal Cells in the Adult Primate CNS: Differential Uptake of DNA-Labeled Precursors," *J. Hirnforsch* 23:23-33 (1983).

Kirschenbaum et al., "Brain-derived Neurotrophic Factor Promotes the Survival of Neurons Arising From the Adult Rat Forebrain Subependymal Zone," *Proc. Nat'l. Acad. Sci.* 92:210-214 (1995).

Kuhn et al., "Epidermal Growth Factor and Fibroblast Growth Factor-2 Have Different Effects on Neural Progenitors in the Adult Rat Brain," *J. Neurosci.* 17(15):5820-5829 (1997).

Leventhal et al., "Endothelial Trophic Support of Neuronal Production and Recruitment from the Adult Mammalian Subependyma," *Molec. Cell. Neurosci.* 13:450-464 (1999).

Lindsay et al., "Neurotrophic Factors: From Molecule to Man," *Trends in Neurosciences* 17(5):182-190 (1994).

Lois et al., "Chain Migration of Neuronal Precursors," *Science* 271:978-981 (1996).

Magavi et al., "Induction of Neurogenesis in the Neocortex of Adult Mice," *Nature* 405:951-955 (2000).

Menezes et al., "The Division of Neuronal Progenitor Cells During Migration in the Neonatal Mammalian Forebrain," *Mol. Cell. Neurosci.* 6:496-508 (1995).

Mizisin et al., "BDNF Attenuates Functional and Structural Disorders in Nerves of Galactose-fed Rats," *J. Neuropathol. & Exp. Neurol.* 56:1290-1301 (1997).

Palmer et al., "Fibroblast Growth Factor-2 Activates a Latent Neurogenic Program in Neural Stem Cells from Diverse Regions of the Adult CNS," *J. Neurosci.* 19(19):8487-8497 (1999).

Palmer et al., "FGF-2-Responsive Neuronal Progenitors Reside in Proliferative and Quiescent Regions of the Adult Rodent Brain," *Mol. Cell, Neurosci.* 6:474-486 (1995).

Pencea et al., "Infusion of BDNF Into the Lateral Ventricle of the Adult Rat Leads to an Increase in the Number of Newly Generated Cells in the Fore, Mid and Hindbrain Parenchyma," *Soc. Neurosci.* 25:2045 (1999) (Abstract only).

Reynolds et al, "Generation of Neurons and Astrocytes from Isolated Cells of the Adult Mammalian Central Nervous System," *Science* 255:1707-1710 (1992).

Richards et al., "*De Novo* Generation of Neuronal Cells from the Adult Mouse Brain," *Proc. Nat'l. Acad. Sci.* 89:8591-8595 (1992).

Roy et al., "Identification, Isolation, and Promoter-Defined Separation of Mitotic Oligodendrocyte Progenitor Cells from the Adult Human Subcortical White Matter," *J. Neurosci.* 19(22):9986-9995 (1999).

Roy et al., "*In Vitro* Neurogenesis by Progenitor Cells Isolated from the Adult Human Hippocampus," *Nature Medicine* 6(3):271-277 (2000).

Vescovi et al., "bFGF Regulates the Proliferative Fate of Unipotent (Neuronal) and Bipotent (Neuronal/Astrogl ial) EGF-Generated CNS Progenitor Cells," *Neuron* 11:951-966 (1993).

Wang et al., "Cortical Interneurons Upregulate Neurotrophins *In Vivo* in Response to Targeted Apoptotic Degeneration of Neighboring Pyramidal Neurons," *Exp. Neurol.* 154:389-402 (1998).

Wang et al., "Isolation of Neuronal Precursors by Sorting Embryonic Forebrain Transfected Regulated by the T α 1 Tubulin Promoter," *Nat. Biotechnol.* 16(2):196-201 (1998).

Yoon et al., "Adenovirus-Mediated Gene Delivery into Neuronal Precursors of the Adult Mouse Brain," *Proc. Nat'l. Acad. Sci.* 93:11974-11979 (1996).

McDonald et al., "A Structural Superfamily of Growth Factors Containing a Cystine Knot Motif," *Cell* 73:421-424 (1993).

Lim et al., "Noggin Antagonizes BMP Signaling to Create a Niche for Adult Neurogenesis," *Neuron* 28:713-726 (2000).

Zimmerman et al., "The Spemann Organizer Signal noggin Binds and Inactivates Bone Morphogenetic Protein 4," *Cell* 86:599-606 (1996).

Gritti et al., "Multipotential Stem Cells from the Adult Mouse Brain Proliferate and Self-Renew in Response to Basic Fibroblast Growth Factor," *J. Neurosci.* 16:1091-1100 (1996).

Gloster et al., "The Tα 1 α-Tubulin Promoter Specifies Gene Expression as a Function of Neuronal Growth and Regeneration in Transgenic Mice," *J. Neurosci.* 14(12): 7319-7330 (1994).

Lothian et al., "An Evolutionarily Conserved Region in the Second Intron of the Human Nestin Gene Directs Gene Expression to CNS Progenitor Cells and to Early Neural Crest Cells," *Eur. J. Neurosci.* 9:452-462 (1997).

Weiss et al., "Is There a Neural Stem Cell in the Mammalian Forebrain?", *TINS* 19:387-393 (1996).

Gould et al., "Proliferation of Granule Cell Precursors in the Dentate Gyrus of Adult Monkeys is Diminished by Stress," *Proc. Natl. Acad. Sci. USA* 95:3168-3171 (1998).

Eriksson et al., "Neurogenesis in the Adult Human Hippocampus," *Nature Medicine* 4:1313-1317 (1998).

Pincus et al., "Neural Stem and Progenitor Cells: A Strategy for Gene Therapy and Brain Repair," *Neurosurgery* 42(4): 858-867 (1998).

Roy et al., "Promoter-Targeted Selection and Isolation of Neural Progenitor Cells From the Adult Human Ventricular Zone," *J. Neurosci. Res.* 59:321-331 (2000).

Brüstle et al., "Chimeric Brains Generated by Intraventricular Transplantation of Fetal Human Brain Cells Into Embryonic Rats," *Nature Biotech.* 16:1040-1044 (1998).

Flax et al., "Engraftable Human Neural Stem Cells Respond to Developmental Cues, Replace Neurons, and Express Foreign Genes," *Nature Biotech.* 16:1033-1039 (1998).

Frederiksen et al., "Proliferation and Differentiation of Rat Neuroepithelia 1 Precursor Cells In Vivo," *J. Neurosci.* 8:1144-1151 (1988).

Fricker et al., "Site-Specific Migration and Neuronal Differentiation of Human Neural Progenitor Cells After Transplantation In the Adult Rat Brain," *J. Neurosci.* 19: 5990-6005 (1999).

Menezes et al., "Expression of Neuron-Specific Tubulin Defines a Novel Population in the Proliferative Layers of the Developing Telencephalon," *J. Neurosci* 14:5399-5416 (1994).

Miller et al., "Isotypes of α-Tubulin are Differentially Regulated During Neuronal Maturation," *J. Cell Biology* 105(No. 6, Pt. 2):3065-3073 (1987).

Miller et al., "Rapid Induction of the Major Embryonic α-Tubulin mRNA, Tα1, During Nerve Regeneration in Adult Rats," *J. Neurosci.* 9:1452-1463 (1989).

Morshead et al., "Neural Stem Cells in the Adult Mammalian Forebrain: A Relatively Quiescent Subpopulation of Subependymal Cells," *Neuron* 13:1071-1082 (1994).

Pincus et al., "Fibroblast Growth Factor-2/Brain-Derived Neurotrophic Factor-Associated Maturation of New Neurons Generated from Adult Human Subependymal Cells," *Ann. Neurology* 43:576-585 (1998).

Sakakibara et al., "Mouse-Musashi-1, a Neural RNA-Binding Protein Highly Enriched in the Mammalian CNS Stem Cell," *Dev. Biol.* 176:230-242 (1996).

Sakakibara et al., "Expression of Neural RNA-Binding Proteins in the Postnatal CNS: Implications of Their Roles in Neuronal and Glial Cell Development," *J. Neurosci.* 17(21):8300-8312 (1997).

Svendsen et al., "Long-Term Survival of Human Central Nervous System Progenitor Cells Transplanted into a Rat Model of Parkinson's Disease," *Exp. Neurol.* 148:135-146 (1997).

Uchida et al., "Direct Isolation of Human Central Nervous System Stem Cells," *Proc. Natl. Acad. Sci.* 97(26):14720-14725 (2000).

Vescovi et al, "Isolation and Cloning of Multipotential Stem Cells From the Embryonic Human CNS and Establishment of Transplantable Human Stem Cells Lines by Epigenetic Stimulation," *Exp. Neurol.* 156:71-83 (1999).

Wang et al., "Promoter-Based Isolation and Fluorescence-Activated Sorting of Mitotic Neuronal Progenitor Cells From the Adult Mammalian Ependymal/Subependymal Zone," *Dev. Neurosci.* 22:167-176 (2000).

Barami et al., "Hu Protein as an Early Marker of Neuronal Phenotypic Differentiation by Subependymal Zone Cells of the Adult Songbird Forebrain," *J. Neurobiol.* 28(1):82-101 (1995).

Rossant et al., "Expression of a Retinoic Acid Response Element-hsplacZ Transgene Defines Specific Domains of Transcriptional Activity During Mouse Embryogenesis," *Genes Dev.* 5:1333-1344 (1991).

Graham et al., "Manipulation of Adenovirus Vector," *Methods of Molecular Biology: Gene Transfer and Expression Protocols*, E. Murray, ed. The Humana Press, Clifton, NJ, pp. 109-128 (1991).

Anderson et al., "A Bipotential Neuroendocrine Precursor Whose Choice of Cell Fate is Determined by NGF and Glucocorticoids," *Cell* 47:1079-1090 (1986).

Barres et al., "A Crucial Role for Neurotrophin-3 in Oligodendrocyte Development," *Nature* 367:371-375 (1994).

Dahlstrand et al., "Characterization of the Human Nestin Gene Reveals a Close Evolutionary Relationship to Neurofilaments," *J. Cell Sci.* 103:589-597 (1992).

DiCicco-Bloom et al., "NT-3 Stimulates Sympathetic Neuroblast Proliferation by Promoting Precursor Survival," *Neuron* 11:1101-1111 (1993).

Goldman, "Adult Neurogenesis: From Canaries to the Clinic," *J. Neurobiol.* 36:267-286 (1998).

Lu et al., "A Paradigm for Distinguishing the Roles of Mitogenesis and Trophism in Neuronal Precursor Proliferation," *Dev. Brain Res.* 94:31-36 (1996).

Sieber-Blum, "Role of the Neurotrophic Factors BDNF and NGF in the Commitment of Pluripotent Neural Crest Cells," *Neuron* 6:949-955 (1991).

Weiss et al., "Multipotent CNS Stem Cells are Present in the Adult Mammalian Spinal Cord and Ventricular Neuroaxis," *J. Neurosci.*, 16(23):7599-7609 (1996).

Pencea et al., "Infusion of Brain-Derived Neurotrophic Factor into the Lateral Ventricle of the Adult Rat Leads to New Neurons in the Parenchyma of the Striatum, Septum, Thalamus, and Hypothalamus," *J. of Neuroscience* 21(17): 6706-6717 (2001).

Chalfie et al., "Green Fluorescent Protein as a Marker for Gene Expression," *Science* 263:802-805 (1994).

Luskin et al., "Neuronal Progenitor Cells Derived from the Anterior Subventricular Zone of the Neonatal Rat Forebrain Continue to Proliferate *In vitro* and Express Neuronal Phenotype," *Molecular and Cellular Neuroscience* 8:351-366 (1997).

Benraiss et al., "Adenoviral Transduction of the Ventricular Wall with a BDNF Expression Vector Induces Neuronal Recruitment from Endogenous Progenitor Cells in the Adult Forebrain," The Third Annual Meeting of the American Society of Gene Therapy, Colorado Convention Center, Denver, Colorado (May 1, 2000).

Kahn et al, "Thérapie Génique des Maladies Neurologiques, " *C.R. Soc. Biol.* 190:9-11 (1996).

Benraiss et al., "Adenoviral Brain-Derived Neurotrophic Factor Induces Both Neostriatal and Olfactory Neuronal Recruitment From Endogenous Progenitor Cells in the Adult Forebrain," *The Journal of Neuroscience* 21(17):6718-6731 (2001).

Nunes et al., "Identification and Isolation of Multipotential Neural Progenitor Cells from the Subcortical White Matter of the Adult Human Brain," *Nature Medicine* 9(4):439-447 (2003).

Brüstle et al., "*In vitro*-Generated Neural Precursors Participate in Mammalian Brain Development," *Proc. Natl. Acad. Sci. USA* 94:14809-14814 (1997).

Azizi et al., "Engraftment and Migration of Human Bone Marrow Stromal Cells Implanted in the Brains of Albino Rats-Similarities to Astrocyte Grafts," *Proc. Natl. Acad. Sci. USA* 95:3908-3913 (1998).

"CytoTherapeutics' Researchers First to Directly Isolate Normal Human Stem Cells," BW Health Wire News Release (Nov. 2, 1999), Reprint from Yahoo! Finance, date unknown.

Goldman et al., "Strategies Utilized by Migrating Neurons of the Postnatal Vertebrate Forebrain," *Trends in Neurosci.* 21(3):107-114 (1998).

Roy et al., "Promoter-Targeted Selection and Isolation of Neural Progenitor Cells From the Adult Human Ventricular Zone," *Journal of Neuroscience Research* 59:321-331 (2000).

Bachiller et al., "The Organizer Factors Chordin and Noggin are Required for Mouse Forebrain Development," *Nature* 403:658-661 (2000).

Gross et al., "Bone Morphogenetic Proteins Promote Astroglial Lineage Commitment by Mammalian Subventricular Zone Progenitor Cells," *Neuron* 17:595-606 (1996).

Li et al., "Neuronal Differentiation of Precursors in the Neocortical Ventricular Zone is Triggered by BMP," *J. Neurosci.* 18:8853-8862 (1998).

Li et al., "Noggin is a Negative Regulator of Neuronal Differentiation in Developing Neocortex," *Dev. Neurosci.* 22:68-73 (2000).

Mehler et al., "Developmental Changes in Progenitor Cell Responsiveness to Bone Morphogenetic Proteins Differentially Modulate Progressive CNS Lineage Fate," *Dev. Neurosci.* 22:74-85 (2000).

Mehler et al., "Cytokines Regulate the Cellular Phenotype of Developing Neural Lineage Species," *Int. J. Dev. Neurosci.* 13:213-240 (1995).

Menezes et al., "The Division of Neuronal Progenitor Cells During Migration in the Neonatal Mammalian Forebrain," *Mol. Cell. Neurosci.* 6:496-508 (1995).

Morshead et al., "Postmitotic Death is the Fate of Constitutively Proliferating Cells in the Subependymal Layer of the Adult Mouse Brain," *J. Neurosci.* 12:249-256 (1992).

Paine-Saunders et al., "Heparan Sulfate Proteoglycans Retain Noggin at the Cell Surface: A Potential Mechanism for Shaping Bone Morphogenetic Protein Gradients," *J. Biol. Chem.* 277:2089-2096 (2002).

Panchision et al., "Sequential Actions of BMP Receptors Control Neural Precursor Cell Production and Fate," *Genes & Dev.* 15:2094-2110 (2001).

Valenzuela et al., "Identification of Mammalian Noggin and Its Expression in the Adult Nervous System," *J. Neurosci.* 15:6077-6084 (1995).

* cited by examiner

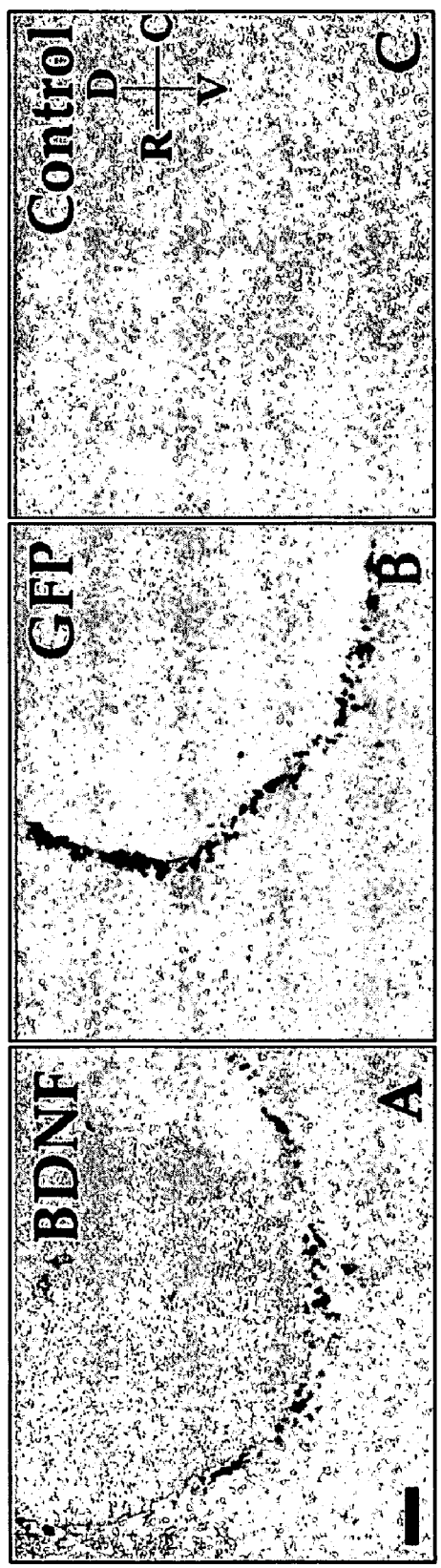

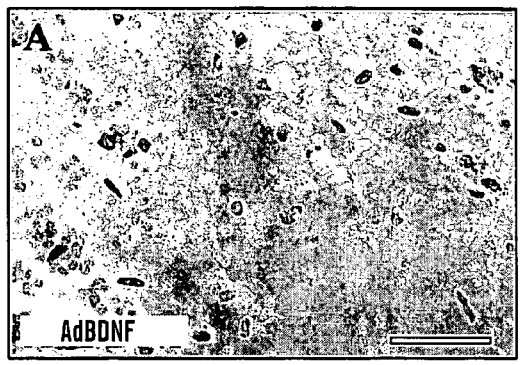 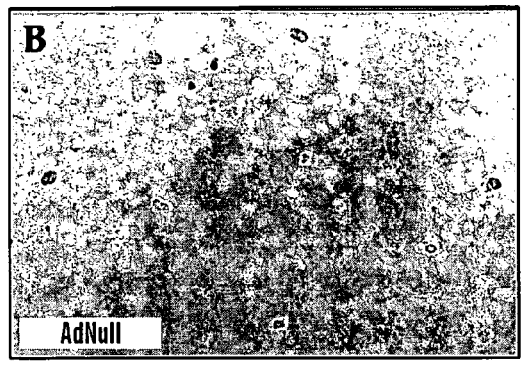
FIG. 5A  FIG. 5B
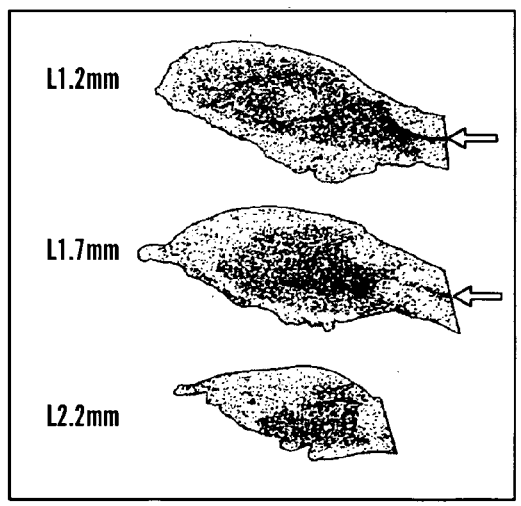 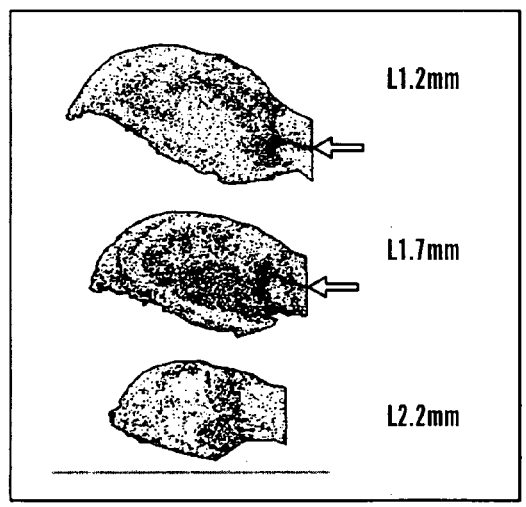
FIG. 5C  FIG. 5D

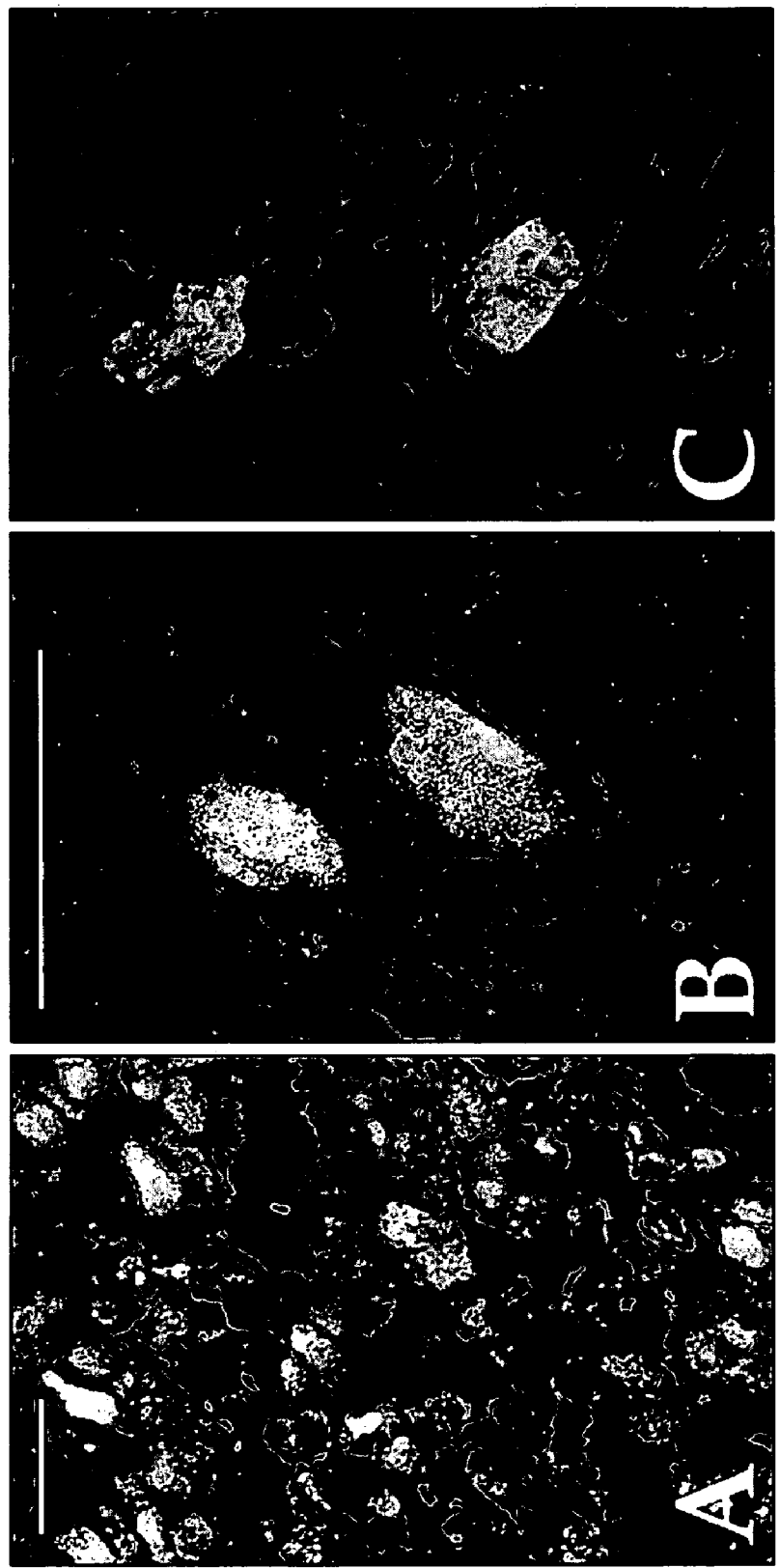

METHOD OF INDUCING NEURONAL PRODUCTION IN THE BRAIN AND SPINAL CORD

This application claims the benefit of U.S. Provisional Patent Application Ser. No. 60/201,230, filed May 1, 2000.

This invention was developed with government funding by NIH Grants P50HL59312, RO1NS29813, and RO1NS33106. The U.S. Government may have certain rights.

FIELD OF THE INVENTION

The present invention relates to a method of inducing neuronal production in the brain and spinal cord.

BACKGROUND OF THE INVENTION

Neural progenitor cells persist throughout the adult forebrain ventricular zone, and have been found in species ranging from canaries to humans (Alvarez-Buylla et al., "Neuronal Stem Cells in the Brain of Adult Vertebrates," *Stem Cells* 13:263–72, (1995); Goldman, S. et al., "Neuronal Precursor Cells of the Adult Rat Ventricular Zone Persist into Senescence, with No Change in Spatial Extent or BDNF Response," *J. Neurobiology* 32:554–566 (1997); Goldman, S. et al., "Neural Precursors and Neuronal Production in the Adult Mammalian Forebrain," *Ann. N.Y. Acad. Sci.* 835: 30–55 (1997); Goldman, S. A. et al., "Strategies Utilized by Migrating Neurons of the Postnatal Vertebrate Forebrain," *Trends in Neurosciences* 21:107–114 (1998)). To the extent that neurogenesis and oligoneogenesis by these endogenous progenitors may be induced or supported exogenously, these cells may provide a cellular substrate for repair in the adult central nervous system (CNS). In culture, adult-derived progenitors have been found to respond to mitogens, in particular epidermal growth factor (EGF) and fibroblast growth factor 2 (FGF2), with increased division and neuronal mitogenesis (Palmer, T. D. et al, "FGF-2-Responsive Neuronal Progenitors Reside in Proliferative and Quiescent Regions of the Adult Rodent Brain," *Mol. Cell Neurosci.* 6:474–86 (1995); Reynolds, B. A. et al, "Generation of Neurons and Astrocytes from Isolated Cells of the Adult Mammalian Central Nervous System," *Science* 255:1707–10 (1992); Richards, L. J. et al, "De Novo Generation of Neuronal Cells from the Adult Mouse Brain," *Proc. Nat'l. Acad. Sci. USA* 89:8591–5 (1992); Vescovi, A. L. et al, "bFGF Regulates the Proliferative Fate of Unipotent (neuronal) and Bipotent (neuronal/astroglial) EGF-generated CNS Progenitor Cells," *Neuron* 11:951–66, (1993)). Furthermore, neurons generated from them respond to brain-derived neurotrophic factor (BDNF) with enhanced migration, maturation, and survival in vitro (Goldman, S. et al., "Neuronal Precursor Cells of the Adult Rat Ventricular Zone Persist into Senescence, with No Change in Spatial Extent or BDNF Response," *J. Neurobiology* 32:554–566 (1997); Goldman, S. et al., "Neural Precursors and Neuronal Production in the Adult Mammalian Forebrain," *Ann. N.Y. Acad. Sci.* 835:30–55 (1997); Kirschenbaum, B. et al, "Brain-derived Neurotrophic Factor Promotes the Survival of Neurons Arising from the Adult Rat Forebrain Subependymal Zone," *Proc. Nat'l. Acad. Sci. USA* 92:210–4 (1995)). Similarly, infusions of EGF and FGF2 into the adult ventricular system stimulate mitotic gliogenesis and neurogenesis respectively (Craig, C. G. et al., "In Vivo Growth Factor Expansion of Endogenous Subependymal Neural Precursor Cell Populations in the Adult Mouse Brain," *J. Neuroscience* 16:2649–58 (1996); Kuhn, H. G. et al, "Epidermal Growth Factor and Fibroblast Growth Factor-2 Have Different Effects on Neural Progenitors in the Adult Rat Brain," *J. Neuroscience* 17:5820–5829 (1997)), while intraventricular infusions of BDNF can enhance neuronal migration to the olfactory bulb, rostral migratory stream and adjacent forebrain (Pencea, V. et al, "Infusion of BDNF into the Lateral Ventricle of the Adult Rat Leads to an Increase in the Number of Newly Generated Cells in the Fore-, Mid- and Hindbrain Parenchyma," *Soc. Neurosci. Abstr.* 25:2045 (1999); Zigova, T. et al, "Intraventricular Administration of BDNF Increases the Number of Newly Generated Neurons in the Adult Olfactory Bulb," *Molec. Cellular Neurosci.* 11:234–245 (1998)). Although intriguing, these studies have been limited by the need for chronic intraventricular catheterization, with its dependence upon protein availability and stability, the uncertain tissue bioavailability of intraventricularly administered proteins, and the risks of infection and catheter loss inherent in chronic ventriculostomy.

The striatum is the major target of the progressive neurodegeneration that occurs in Huntington's Disease, in which the major neuron loss is that of the striatal GABA-producing neurons. Other degenerative diseases, such as amyotrophic lateral sclerosis (ALS; also known as Lou Gehrig's Disease), and progressive muscular atrophy, result at least in part from a decay of motor neurons which are located in the ventral horn of the spinal cord.

While there are some therapies available to treat the symptoms and decrease the severity of such diseases (e.g., L-dopa to treat Parkinson's Disease), there currently exists no effective treatment to prevent or reduce the degeneration of most of the above-mentioned classes of affected neurons, or to promote their repair. Several naturally-occurring proteins have been identified based on their trophic activity on various neurons. These molecules are termed "neurotrophic factors". Neurotrophic factors are endogenous, soluble proteins that can stimulate or regulate the production, survival, growth, and/or morphological plasticity of neurons. (See Fallon and Laughlin, *Neurotrophic Factors,* Academic Press, San Diego, Calif. (1993)).

The known neurotrophic factors belong to several different protein superfamilies of polypeptide growth factors based on their amino acid sequence homology and/or their three-dimensional structure (MacDonald et al., "A Structural Superfamily Of Growth Factors Containing A Cystine Knot Motif," *Cell* 73:421–424 (1993)). One family of neurotrophic factors is the neurotrophin family. This family currently consists of nerve growth factor (NGF), brain derived neurotrophic factor (BDNF), neurotrophin-3 (NT-3), neurotrophin-4 (NT-4), and neurotrophin-6 (NT-6).

On the basis of current studies, and of their limitations in practice, it will be appreciated that a need exists for an efficient means of delivering neurotrophic differentiation agents to the adult ventricular zone, the site of residual progenitor cells in the adult brain. Furthermore, in view of the fact that many nervous system disorders and diseases have no known cure, there is a need in the art for new methods of inducing neuronal production in the adult brain, especially for treating Huntington's Disease and other degenerative neurological conditions, as well as stroke and traumatic brain injury.

The present invention is directed to overcoming these and other deficiencies in the art.

SUMMARY OF THE INVENTION

The present invention relates to a method of inducing neuronal production in post-natal and adult brain and spinal cord. This involves providing a nucleic acid construct encoding a neurotrophic factor and injecting the nucleic acid construct into a subject's lateral ventricles or ventricular zone wall under conditions effective to express the neurotrophic factor and to induce neuronal production in the brain and spinal cord of subject.

The present invention also relates to a method of recruiting neurons to the brain of a subject. This involves providing a nucleic acid construct encoding a neurotrophic factor and injecting the nucleic acid construct into the subject's lateral ventricles or ventricular zone wall under conditions effective to express the neurotrophic factor and to recruit neurons to the brain of the subject.

The present invention also relates to a method of treating a neurodegenerative condition. This involves providing a nucleic acid construct encoding a neurotrophic factor and injecting the nucleic acid construct into a subject's lateral ventricles or ventricular zone wall under conditions effective to treat a neurodegenerative condition.

The present invention also relates to another method of treating a neurodegenerative condition. This involves providing a neurotrophic factor and injecting the neurotrophic factor into a subject's lateral ventricles or ventricular zone wall under conditions effective to treat a neurodegenerative condition.

Previous studies have reported that ependymal cells could express adenovirally-delivered marker genes after intraventricular injection of virus (Bajocchi, G. et al., "Direct In Vivo Gene Transfer to Ependymal Cells in the Central Nervous System Using Recombinant Adenovirus Vectors," *Nature Genetics* 3:229–234 (1993); Yoon, S. et al, "Adenovirus-Mediated Gene Delivery into Neuronal Precursors of the Adult Mouse Brain," *Proc. Nat'l. Acad. Sci. USA* 93:11974–11979 (1996), which are hereby incorporated by reference in their entirety). However, no attempt had ever been made to utilize this strategy to deliver transgenes encoding neurotropic agents to either the ventricular zone, including its subependyma, or the endogenous precursor cells. Due to the high efficiency infection of, and transgene expression by, the adult ependyma, intraventricular delivery of viral vectors can be used for the sustained delivery of neurotrophins not only to the ventricular zone, but also to the CSF, and hence throughout the neuraxis. The present invention provides a method of gene therapy that allows for widespread production of BDNF by ependymal cells lining the ventricular wall which results in the subrogation of the ependyma into a secretory source for BDNF. This, in turn, results in the stimulation of neurogenesis in the injected brain and an expansion of the regions into which new neurons can be added to include areas such as the neostriatum that normally cannot replace lost neurons.

BRIEF DESCRIPTION OF THE DRAWINGS

FIGS. 1A and 1B are sagittal sections of infected rat brain. FIG. 1A shows a single intraventricular injection of an adenoviral vector bearing a green fluorescent protein (GFP) gene, expressed under the control of the constitutive CMV promoter, exhibiting widespread infection of the ventricular ependyma, bilaterally and throughout the ventricular system. FIG. 1B, along the striatal and septal walls, GFP expression is seen to be largely limited to the ventricular surface, with little subependymal and no parenchymal extension. FIG. 1C, a coronal section taken at the level of the main body of the lateral ventricles, again reveals GFP expression by the infected striatal and callosal ventricular surfaces. Unlike the striatal and septal walls, the callosal wall shows subependymal and some parenchymal extension of labeled cells. Abbreviations: Str, striatum; LV, lateral ventricle; CC, corpus callosum. Key: D, dorsal; V, ventral; A, anterior; P, posterior.

In FIGS. 2A and 2B, HeLa cells transduced with AdBDNF secreted BDNF in a viral dose-dependent manner (n=3). In FIGS. 2C and 2D, AdBDNF injected animals showed sustained expression of high levels of BDNF in CSF, as measured on day 20 (n=5). FIGS. 2A and 2C show results in pg/ml, while FIGS. 2B and 2D are given in pg/μg protein. Abbreviation: moi, for multiplicity of infection.

FIGS. 3A–E show AdBDNF transduced expression of BDNF and hGFP mRNA in vivo. Serial sections of AdBDNF-GFP injected brain were treated with antisense probes for BDNF, shown in FIGS. 3A and 3D, or GFP, shown in FIGS. 3B and 3E. mRNA expression was restricted to the wall of the lateral ventricle. FIG. 3C shows a sense probe for BDNF, as control. Legend: d, dorsal; v, ventral; r, rostral; c, caudal. Scale=35 μm.

FIG. 4 is a diagram of the strategy employed to induce adult neuronal recruitment in experimental subjects.

FIGS. 5A–E show that AdBDNF injection increased recruitment to the olfactory bulb. FIG. 5A shows the presence of BrdU+ cells in the olfactory bulbs of subject brain injected with AdBDNF:IRES:hGFP. FIG. 5B shows the presence of BrdU+ cells in the olfactory bulbs of AdNull:GFP-injected brain, at day 20. FIG. 5C shows a stereological reconstruction of BrdU+ cells. Viewed here at different mediolateral levels of the olfactory bulb, FIG. 5C reveals substantially higher BrdU+ cell densities in the olfactory subependyma and granular layers of AdBDNF-treated rats, than in the AdGFP-injected controls, shown in FIG. 5D. Arrows denote entry to rostral migratory stream. FIG. 5E shows that the average number of BrdU+ cells/mm$^3$ in the olfactory bulb (n=4/group), plotted as a function of treatment, again revealing significantly higher numbers of newly generated, BrdU+ cells in AdBDNF-treated rats as compared to control olfactory bulbs.

FIGS. 6A–C shows that AdBDNF-associated newly generated olfactory cells were neurons. Confocal imaging confirmed that BrdU+ cells added to the olfactory bulb were almost entirely neurons, in rats injected with virus 3 weeks before sacrifice, and given BrdU daily until the day before. FIGS. 6A–C show merged z-dimension stacks of confocal images of BrdU co-labeling with β-III tubulin+ (6A and 6B) and MAP-2+ (6C) neurons. This suggests that the AdBDNF-associated increase in the olfactory bulb BrdU labeling index reflected enhanced neurogenesis and/or recruitment to the bulb. Scale=25 µm.

FIG. 8A shows sagittal (left) and coronal (right) schematics of the neostriatal region assessed for neuronal addition, in AdBDNF-injected rats and their AdNull-injected controls. FIG. 8B plots the mean density of β-III-tubulin+/BrdU+ cells in AdBDNF- and AdNull-injected striata, and in PBS-injected controls, at day 20 (n=4).

FIGS. 9A–C show a representative β-III-tubulin+/BrdU+ cell. FIG. 9A is a z-dimension composite of serial 0.9 µm images, showing β-III-tubulin+ and BrdU immunoreactivities. FIG. 9B, is a z-dimension series of 6×0.9 µm confocal images taken 0.6 µm apart, displaying the concurrence of BrdU and β-III-tubulin in the new neuron. FIG. 9C is a single optical section with reconstructed orthogonal images, as viewed from the sides in both the xz and yz planes. In FIGS. 9D-F, another newly generated, β-III-tubulin+/BrdU+ neostriatal neuron (arrow) is seen, similarly viewed as a z-stack composite in FIG. 9D. By way of contrast, this field also includes both a non-neuronal BrdU+ cell, and a β-III-tubulin+ but BrdU-unlabeled resident neuron. Like FIGS. 9A–C, this field is also viewed as a series of optical sections (9E), and in orthogonal side-views (9F). FIGS. 9G–J show a pair of β-III-tubulin+/BrdU+ striatal neurons (arrows), composited in FIG. 9G with split images separately indicating β-III-tubulin+ and BrdU, respectively. FIGS. 9H and 9I, are an optical section with orthogonal images taken at two different points, to allow individual assessment of the β-III-tubulin staining of each of these BrdU+ cells. Both BrdU+ nuclei are completely surrounded by β-III-tubulin. FIG. 9J shows a series of z-dimension optical sections through these cells, again confirming the coincident expression of BrdU and β-III-tubulin. FIGS. 9K–L are low power views of the fields shown in FIGS. 9A–C and 9G–J, respectively, in order to visualize the range of morphologies of both resident (examples as arrowheads) and newly added (arrows) neurons. * in FIG. 9L shows a myelinated bundle passing through the striatal matrix. Scale=10 µm.

FIGS. 10A–C show a typical NeuN+/BrdU+ striatal neuron (arrow); local resident neurons (NeuN+/BrdU−) shown by arrowheads. FIG. 10A shows a z-dimension composite of serial 1 µm images, with split (NeuN) and (BrdU) images on the right. FIG. 10B shows a single optical section with reconstructed orthogonal images, as viewed from the sides in both the xz (top) and yz (right side) planes. FIG. 10C shows a z-dimension series, viewed as 4×0.9 µm optical sections taken 0.6 µm apart. FIG. 10D shows a BrdU+/calbindin+ neuron, with calbindin indicated by the arrow. FIGS. 10E–F show confocal images of a GAD67+/BrdU+ neuron in an AdBDNF-treated striatum. FIG. 10E shows a confocal section with reconstructed orthogonal side-views. In the orthogonal side-views, the BrdU+ nuclei remain completely surrounded by the GAD67 antigen. FIG. 10E shows a z-dimension series of 4 separate 0.9 µm confocal images taken 0.6 µm apart, displayed to reveal the correspondence of BrdU and GAD67 in the same cell at multiple z-levels. FIGS. 10G–I show analogous images of a DARPP32/BrdU+ neuron in the same striatum. FIG. 10G shows the z-dimension composite of serial 0.9 µm images, again with split images to show DARPP32 (arrow) and BrdU staining individually. FIG. 10H shows an optical section with reconstructed orthogonal side-views, as described. In both the xz and yz planes, the BrdU+ nucleus is completely surrounded by DARPP32 signal. FIG. 10I shows a z-dimension series through this cell. All images were taken of striatal sections sampled from AdBDNF-treated rats, sacrificed 3 weeks after virus administration. Scale=10 µm.

FIG. 11 shows AdBDNF-induced striatal neurons matured and survived for at least 5–8 weeks, as demonstrated by β-III-tubulin+/BrdU+, GAD67+/BrdU+, and DARPP32+/BrdU+ striatal neurons persisted in AdBDNF-injected rats. FIG. 11A shows the z-dimension composite of serial 1 µm images, with split images to show β-III-tubulin+ (arrow) and BrdU, respectively. FIG. 11B shows a confocal section with reconstructed orthogonal images, as viewed from the sides in both xz (top) and yz (right side) planes. FIG. 11C shows a z-dimension series of 4 separate 0.9 µm confocal images taken 0.6 µm apart, confirming the β-III-tubulin-immunoreactivity of the BrdU+ cell. FIG. 11G is a z-dimension composite of serial optical sections, showing DARPP32 and BrdU immunoreactivities. DARPP32+/BrdU+ neurons indicated by arrows; BrdU-unlabeled resident neurons indicated by arrowheads. FIG. 11H shows orthogonal views of the DARPP-32+/BrdU+ striatal neuron. FIG. 11I showing serial 0.9 µm optical sections taken 0.6 µm apart, confirms the coincidence of BrdU and DARPP-32 in the same cell. Scale 10 µm.

DETAILED DESCRIPTION OF THE INVENTION

Figure 1B:
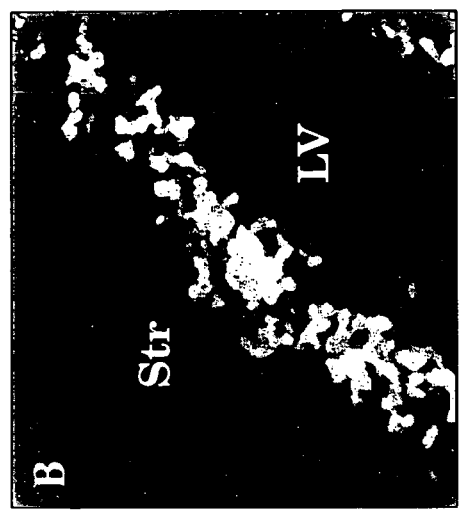
FIGS. 1A–C show the ependymal restriction of intraventricular adenoviral infection.

The present invention relates to a method of inducing neuronal production in post-natal and adult brain and spinal cord. This involves providing a nucleic acid construct encoding a neurotrophic factor and injecting the nucleic acid construct into a subject's lateral ventricles or ventricular zone wall under conditions effective to express the neurotrophic factor and to induce neuronal production in the subject.

Neuronal production as used herein refers to the generation of new neurons. One type of nucleic acid suitable for the present invention are nucleic acids which encode growth factor products, in particular neurotrophic growth factors. Such nucleic acids include, but are not limited to, the nucleic acid encoding BDNF, the neurotrophins NT-3 (Regeneron, Tarrytown, N.Y.) and NT-4/NT-5, insulin-like growth factor, nerve growth factor (NGF), the recently identified neurotrophic family of factors designated "NNT" (see U.S. Pat. No. 6,143,874 to Chang, which is hereby incorporated by reference in its entirety), ciliary neurotrophic factor (CNTF), and the interleukins.

In the brain, a protein known as bone morphogenic protein drives progenitor cells to differentiate into glial cells. Noggin is a developmental molecule which suppresses bone morphogenic protein in the brain. Without the influence of bone morphogenic protein, progenitor cells differentiate into glia cells rather than neurons. Thus, noggin acts to induce neuronal production through its suppression of endogenous bone morphogenic protein (Lim et al., "Noggin Antagonizes BMP Signaling To Create A Niche for Adult Neurogenesis," *Neuron* 28: 713–726 (2000); Zimmerman et al., "The Spemann Organizer Signal Noggin Binds and Inactivates Bone Morphogenetic Protein 4," *Cell* 86: 599–606 (1996), which are hereby incorporated by reference in their entirety). Therefore, the nucleic acid which encodes the neurotrophic factor noggin is suitable for use in the nucleic acid construct of the present invention.

Also suitable for use in the present invention is a nucleic acid which encodes a neurotrophic factor which is an inhibitor of bone morphogenic proteins. These factors are proteins which, like noggin, are capable of suppressing bone morphogenic protein, thereby driving the differentiation of progenitor cells in the brain into neurons. (Lim et al., "Noggin Antagonizes BMP Signaling To Create a Niche for Adult Neurogenesis," *Neuron* 28: 713–726 (2000); Zimmerman et al., "The Spemann Organizer Signal Noggin Binds and Inactivates Bone Morphogenetic Protein 4," *Cell* 86: 599–606 (1996), which are hereby incorporated by reference in their entirety). The suppression of bone morphogenic protein by noggin or noggin-like proteins, as they are also known, may be used effectively in combination or serial addition with BDNF to further increase neuronal production in the brain.

A gene or cDNA encoding the desired neurotrophic factor product or protein, or fragment thereof, may be obtained for example by screening a genomic or cDNA library, or by PCR amplification.

Providing a nucleic acid construct of the present invention involves incorporating the nucleic acid molecules of the present invention into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences. The practice of the present invention will employ, unless otherwise indicated, conventional methods of virology, microbiology, molecular biology, and recombinant DNA techniques within the skill of the art. Such techniques are explained fully in the literature. See, e.g., Sambrook, et al., *Molecular Cloning: A Laboratory Manual* (1989); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Fundamental Virology*, 2nd Edition, vol. I & II (B. N. Fields and D. M. Knipe, eds.), which are hereby incorporated by reference in their entirety.

The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The nucleic acid molecules of the present invention may be inserted into any of the many available expression vectors and cell systems using reagents that are well known in the art.

Examples of viruses which have been employed as vectors for the transduction and expression of exogenous genes in mammalian cells include the SV40 virus (Innis et al., "Chromatin Structure of Simian Virus 40-pBR322 Recombinant Plasmids in COS-1 Cells," *Mol. Cell Biol.* 3(12): 2203–2210 (1983); Okayama et al., "Bacteriophage Lambda Vector for Transducing a cDNA Clone Library into Mammalian Cells," *Mol. Cell Biol.* 5(5):1136–1142 (1985), which are hereby incorporated by reference in their entirety) and bovine papilloma virus (Meneguzzi et al., "Plasmidial Maintenance in Rodent Fibroblasts of a BPV1-pBR322 Shuttle Vector Without Immediately Apparent Oncogenic Transformation of the Recipient Cells," *EMBO J.* 3(2): 365–371 (1984); DiMaio et al., "Bovine Papillomavirus Vector that Propagates as a Plasmid in Both Mouse and Bacterial Cells," *Proc. Nat'l. Acad. Sci. USA* 79(13):4030–4034 (1982); Lusky et al., "Characterization of the Bovine Papilloma Virus Plasmid Maintenance Sequences," *Cell* 36(2):391–401 (1984); Giri et al., "Comparative Studies of the Expression of Linked *Escherichia coli* gpt Gene and BPV-1 DNAs in Transfected Cells," *Virology* 127(2):385–396 (1983), which are hereby incorporated by reference in their entirety), the retrovirus Moloney murine sarcoma virus (Perkins et al., "Design of a Retrovirus-Derived Vector for Expression and Transduction of Exogenous Genes in Mammalian Cells," *Mol. Cell Biol.* 3(6):1123–1132 (1983); Lee et al., "DNA Clone of Avian Fujinami Sarcoma Virus with Temperature-Sensitive Transforming Function in Mammalian Cells," *J. Virol.* 44(1): 401–412 (1982); Curran et al., "FBJ Murine Osteosarcoma Virus: Identification and Molecular Cloning of Biologically Active Proviral DNA," *J. Virol.* 44(2):674–682 (1982); Gazit et al., "Mammalian Cell Transformation by a Murine Retrovirus Vector Containing the Avian Erythroblastosis Virus erbB Gene," *J. Virol.* 60(1):19–28 (1986), which are hereby incorporated by reference in their entirety), and HIV-based viruses.

A number of adenovirus (Ad) based gene delivery systems have also been developed. Human adenoviruses are double-stranded DNA viruses which enter cells by receptor-mediated endocytosis. These viruses are particularly well suited for gene therapy, because they are easy to grow and manipulate and they exhibit a broad host range in vivo. Adenovirus is easily produced at high titers and is stable so that it can be purified and stored. Even in the replication-competent form, adenoviruses generally cause only low level morbidity and are not associated with human malignancies. Furthermore, Ad infects both dividing and non-dividing cells; a number of tissues which are targets for gene therapy comprise largely non-dividing cells (U.S. Pat. No. 6,171,855 to Askari, which is hereby incorporated by reference in its entirety). For descriptions of various adenovirus-based gene delivery systems, see, e.g., Haj-Ahmad et al., "Development of a Helper-Independent Human Adenovirus Vector and Its Use in the Transfer of the Herpes Simplex Virus Thymidine Kinase Gene," *J. Virol.* 57(1):267–274 (1986); Bett et al., "Packaging Capacity and Stability of Human Adenovirus Type 5 Vectors," *J. Virol.* 67(10):5911–5921 (1993); Mittereder et al., "Evaluation of the Efficacy and Safety of in vitro, Adenovirus-Mediated Transfer of the Human Cystic Fibrosis Transmembrane Conductance Regulator cDNA," *Hum. Gene Ther.* 5(6): 717–729 (1994); Seth et al., "Mechanism of Enhancement of DNA Expression Consequent to Cointernalization of a Replication-Deficient Adenovirus and Unmodified Plasmid DNA," *J. Virol.* 68(2):933–940 (1994); Barr et al., "Efficient Catheter-Mediated Gene Transfer into the Heart Using Replication-Defective Adenovirus," *Gene Ther.* 1(1):51–58 (1994); Berkner et al., "Development of Adenovirus Vectors for the Expression of Heterologous Genes," *Biotechniques* 6(7):616–629 (1988); Rich et al., "Development and Analysis of Recombinant Adenoviruses for Gene Therapy of Cystic Fibrosis," *Hum. Gene Ther.* 4(4):461–476 (1993), which are hereby incorporated by reference in their entirety.

Retroviral vectors, capable of integration into the cellular chromosome, have also been used for the identification of developmentally important genes via insertional mutagenesis (see, e.g., U.S. Pat. No. 6,207,455 to Chang, which is hereby incorporated by reference in its entirety). Retroviral vectors are also used in therapeutic applications (e.g., gene therapy), in which a gene (or genes) is added to a cell to replace a missing or defective gene or to inactivate a pathogen such as a virus. The members of the family Retroviridae are characterized by the presence of reverse transcriptase in their virions (U.S. Pat. No. 6,207,344 to Chang, which is hereby incorporated by reference in its entirety). The family is divided into three subfamilies: (1) Oncovirinae, including all the oncogenic retroviruses, and several closely related non-oncogenic viruses; (2) Lentivirinae, the "slow retroviruses," discussed in greater detail below, and (3) Spumavirinae, the "foamy" retroviruses that induce persistent infections, generally without causing any clinical disease (U.S. Pat. No. 6,218,181 to Verma et al., which is hereby incorporated by reference in its entirety). Some of the retroviruses are oncogenic (i.e., tumorigenic), while others are not. The oncoviruses induce sarcomas, leukemias, lymphomas, and mammary carcinomas in susceptible species (U.S. Pat. No. 6,033,905 to Wilson et al., which is hereby incorporated by reference in its entirety). Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy. For example, the majority of the approved gene transfer trials in the United States rely on replication-defective retroviral vectors harboring a therapeutic polynucleotide sequence as part of the retroviral genome (Miller et al., "Gene Transfer by Retrovirus Vectors Occurs Only in Cells that are Actively Replicating At The Time of Infection," *Mol. Cell Biol.* 10(8):4239–4442 (1990); Cornetta et al., "No Retroviremia or Pathology in Long-term Follow-up of Monkeys Exposed to Amphotropic Retrovirus," *Hum. Gene Ther.* 2(3):215–219 (1991), which are hereby incorporated by reference in their entirety). As is known in the art, the major advantages of retroviral vectors for gene therapy are the high efficiency of gene transfer into certain types of replicating cells, the precise integration of the transferred genes into cellular DNA, and the lack of further spread of the sequences after gene transfer (U.S. Pat. No. 6,033,905 to Wilson et al., which is hereby incorporated by reference in its entirety).

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visnamaedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). Lentivirus virions have bar-shaped nucleoids and contain genomes that are larger than other retroviruses. Lentiviruses use tRNA$^{lys}$ as primer for negative-strand synthesis, rather than the tRNA$^{pro}$ commonly used by other infectious mammalian retroviruses. The lentiviral genomes exhibit homology with each other, but not with other retroviruses (Davis et al., *Microbiology*, 4th ed., J. B. Lippincott Co., Philadelphia, Pa., pp. 1123–1151 (1990), which is hereby incorporated by reference in its entirety). An important factor in the disease caused by these viruses is the high mutability of the viral genome, which results in the production of mutants capable of evading the host immune response. The advantage of lentiviruses is the ability for sustained transgene expression. Thus, in one embodiment of the present invention, a lentiviral vector is employed to provide long-term expression of the neurotrophic transgene in a target cell.

Adeno-associated viruses (AAV) may also be employed as a vector in the present invention. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep62, and rep40) are involved in replication, rescue, and integration of the AAV genome. The cap proteins (VP1, VP2, and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene (B. J. Carter, in "*Handbook of Parvoviruses*", ed., P. Tijsser, CRC Press, pp. 155–168 (1990), which is hereby incorporated by reference in its entirety). It has been shown that the ITRs represent the minimal sequence required for replication, rescue, packaging, and integration of the AAV genome (U.S. Pat. No. 5,871,9982 to Wilson et al., which is hereby incorporated by reference in its entirety).

As noted above, viral vectors have been successfully employed in order to increase the efficiency of introducing a recombinant vector into suitably sensitive host cells. Therefore, viral vectors are particularly suited for use in the present invention, including any adenoviral (Ad), retroviral, lentiviral, or adeno-associated viral (AAV) vectors described above or known in the art. Current research in the field of viral vectors is producing improved viral vectors with high-titer and high-efficiency of transduction in mammalian cells (see, e.g., U.S. Pat. No. 6,218,187 to Finer et al., which is hereby incorporated by reference in its entirety). Such vectors are suitable in the present invention, as is any viral vector that comprises a combination of desirable elements derived from one or more of the viral vectors described herein. It is not intended that the expression vector be limited to a particular viral vector.

Certain "control elements" or "regulatory sequences" are also incorporated into the vector-construct. The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription, and translation of a coding sequence in a recipient cell. Not all of these control elements need always be present so long as the selected coding sequence is capable of being replicated, transcribed, and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcriptional control signals in eukaryotes comprise "promoter" and "enhancer" elements. Promoter and enhancer elements have been isolated from a variety of eukaryotic sources, including genes in yeast, insect, and mammalian cells, and viruses. Analogous control elements, i.e., promoters, are also found in prokaryotes. Such elements may vary in their strength and specificity. For example, promoters may be "constitutive" or "inducible."

A constitutive promoter is a promoter that directs expression of a gene throughout the development and life of an organism. Examples of some constitutive promoters that are widely used for inducing expression of transgenes include the nopoline synthase (NOS) gene promoter from *Agrobacterium tumefaciens* (U.S. Pat. No. 5,034,322 to Rogers et al., which is hereby incorporated by reference in its entirety), the cytomegalovirus (CMV) early promoter, those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, or a physiological stress directly imposed upon the organism such as cold, heat, toxins, or through the action of a pathogen or disease agent. A recombinant cell containing an inducible promoter may be exposed to an inducer by externally applying the inducer to the cell or organism by exposure to the appropriate environmental condition or the operative pathogen.

Inducible promoters may be used in the viral vectors of this invention. These promoters will initiate transcription only in the presence of an additional molecule. Examples of inducible promoters include the tetracycline response element and promoters derived from the β-interferon gene, heat shock gene, metallothionein gene or any obtainable from steroid hormone-responsive genes. Tissue specific expression has been well characterized in the field of gene expression and tissue specific and inducible promoters are well known in the art. These genes are used to regulate the expression of the foreign gene after it has been introduced into the target cell.

Another type of promoter suitable for the present invention is a cell specific promoter. "Specific," as used herein to describe a promoter, means that the promoter permits substantial transcription of the DNA only in a predetermined, or "chosen" cell type. A chosen cell type can refer to different types of cells, or different stages in the developmental cycle of a cell. An example of a cell specific promoter useful in the present invention is the nestin enhancer (E/nestin). This derives from the 637 bp-region between bases 1162 and 1798 of the second intronic enhancer of the rat nestin gene, which is evolutionarily conserved between human and rat. E/nestin is sufficient to control gene expression in CNS neuroepithelial progenitor cells (Lothian et al., "An Evolutionarily Conserved Region in the Second Intron of the Human Nestin Expression to CNS Progenitor Cells and to Early Neural Crest Cells," *Eur. J. Neurosci.* 9(3):452–462 (1997), Roy et al., "Promoter Targeted Selection and Isolation of Neural Progenitor Cells from Adult Human Ventricular Zone," *J. Neurosci. Research* 59: 321–331 (2000), which are hereby incorporated by reference in their entirety). In one aspect of the present invention, the nestin enhancer is placed upstream to a basal promoter in order to drive gene expression specifically in neural precursor cells. Another example of a cell specific promoter suitable for the present invention is the Tα1 tubulin promoter, which uses a regulatory sequence neuronal progenitor cell using a regulatory sequence expressed only in neuronal progenitor cells and young neurons (Roy et al., "In vitro Neurogenesis by Neural Progenitor Cells Isolated From the Adult Human Hippocampus," *Nature Medicine:* 6, 271–277 (2000); (Wang et al., "Isolation of Neuronal Precursors by Sorting Embryonic Forebrain Transfected Regulated by the T Alpha 1 Tubulin Promoter," *Nat. Biotechnol.* 16(2):196–201 (1998), which are hereby incorporated by reference in their entirety). Also suitable in the present invention are promoters of the musashi gene ( Good et al., "The Human Musashi Homologue 1 (MSI1) Gene Encoding the Homologue of musashi/Nrp-1, A Neural RNA-Binding Protein Putatively Expressed in CNS Stem Cells And Neuroprogenitors Cells," *Genomics* 52:382–384 (1998), which is hereby incorporated by reference in its entirety), the SOX2 gene (Zapponi et al., "SOX2 Regulatory Sequences: Direct Expression of a β-geo Transgene to Telencephalic Neural Stem Cells and Precursors of Mouse Embryo Revealing Regionalization of Gene Expression in CNS Stem Cells," *Development* 127:2368–2382 (2000), which is hereby incorporated by reference in its entirety), and the neurogenin gene (Simmons, et al., "Neurogenin2 Expression in Ventral and Dorsal Spinal Neural Tube Progenitor Cells is Regulated by Distinct Enhancers," *Developmental Biol.* 229: 327–339 (2001), which is hereby incorporated by reference in its entirety), each of which is specific for neuroprogenitor cells at different stages of their development.

It will be appreciated by those skilled in the art that any number of suitable transcriptional regulatory elements may be used to direct specific cell-type gene expression the present invention. Selection will be highly dependent upon the vector system and host utilized.

Cell specific promoters are particularly preferable in the present invention, because they provide a second level of control over transgene expression, in addition to that of selective transduction by the vector. The most frequently used promoters are viral in origin, often derived from a different virus than the vector backbone, for example cytomegalovirus promoters have been used in all vector systems. Viral promoters have the advantages of being smaller, stronger, and better understood than most human promoter sequences.

To ensure efficient expression, 3' polyadenylation regions must be present to provide for proper maturation of the mRNA transcripts. The native 3'-untranslated region of the gene of interest is preferably used, but the polyadenylation signal from, for example, SV40, particularly including a splice site, which provides for more efficient expression, could also be used. Alternatively, the 3'-untranslated region derived from a gene highly expressed in a particular cell type could be fused with the gene of interest.

The vector of choice, a suitable marker gene, promoter/enhancer region(s), and an appropriate 3' regulatory region can be operably ligated together to produce the expression system of the present invention, or suitable fragments thereof, using well known molecular cloning techniques as described in Sambrook et al., *Molecular Cloning: A Laboratory Manual,* Second Edition, Cold Spring Harbor Press, NY (1989), and Ausubel et al. (1989) *Current Protocols in Molecular Biology,* John Wiley & Sons, New York, N.Y., which are hereby incorporated by reference in their entirety. The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner that a functional protein is produced.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

An example of a marker suitable for the present invention is the green fluorescent protein (GFP) gene. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (Prasher et al., "Primary Structure of the Aequorea Victoria Green-Fluorescent Protein," *Gene* 111(2):229–233 (1992); U.S. Pat. No. 5,491,084 to Chalfie et al., which are hereby incorporated by reference in their entirety). A plasmid encoding the GFP of *Aequorea victoria* is available from the ATCC as Accession No. 75547. Mutated forms of GFP that emit more strongly than the native protein, as well as forms of GFP amenable to stable translation in higher vertebrates, are commercially available from Clontech Laboratories, Inc. (Palo Alto, Calif.) and can be used for the same purpose. The plasmid designated pTα1-GFPh (ATCC Accession No. 98299) includes a humanized form of GFP. Indeed, any nucleic acid molecule encoding a fluorescent form of GFP can be used in accordance with the subject invention. Standard techniques are then used to place the nucleic acid molecule encoding GFP under the control of the chosen cell specific promoter.

Markers are also suitable for assessing neuronal production following injection. An exemplary marker for this purpose is the mitotic marker bromodeoxyuridine (BrdU). The subject can be injected with BrdU, which is indicative of DNA replication in cells, simultaneously or following the injection of the nucleic acid-viral vector of the present invention. Similarly, markers specific for neurogenesis, or neuronal production, can also be assessed in spinal cord by ELISA of the subject's CSF for the appropriate neurotrophic factor. Also suitable are markers which are indicative of the stage of development of a cell, for example, the NeuN gene, which is expressed only by mature neurons.

The selection marker employed will depend on the target species and/or host or packaging cell lines compatible with a chosen vector.

Once the nucleic acid construct of the present invention has been prepared and inserted into the desired vector, it is ready to be incorporated into a host cell. Basically, this method is carried out by transforming a host cell with a nucleic construct of the present invention under conditions effective to yield transcription of the DNA molecule in the host cell, using standard cloning procedures known in the art, such as that described by Sambrook et al., *Molecular Cloning: A Laboratory Manual,* Second Edition, Cold Springs Laboratory, Cold Springs Harbor, N.Y. (1989), which is hereby incorporated by reference in its entirety. Suitable hosts include, but are not limited to, bacteria, virus, yeast, mammalian cells, insect, plant, and the like. Where the vector is a viral vector, the host cell is chosen to optimize packaging, where required, and titer. For example, where the nucleic acid of the present invention is inserted into an adenovirus vector, the cell line HEK293 is an appropriate host line, with the expectation of high vector progeny titers. The vector DNA may be introduced into the packaging cell by any of a variety of transfection techniques, e.g., calcium phosphate coprecipitation, electroporation, etc. (See, e.g., Sambrook, et al., *Molecular Cloning: A Laboratory Manual* (1989); *DNA Cloning: A Practical Approach,* vol. I & II (D. Glover, ed.); *Oligonucleotide Synthesis* (N. Gait, ed., Current Edition); *Nucleic Acid Hybridization* (B. Hames & S. Higgins, eds., Current Edition); *Fundamental Virology,* 2nd Edition, vol. I & II (B. N. Fields and D. M. Knipe, eds.), which are hereby incorporated by reference in their entirety.) Other conventional methods employed in this invention include homologous recombination of the viral genomes, plaquing of viruses in agar overlay, methods of measuring signal generation, and the like known in the art or described in literature.

Following transfection of an appropriate host with the viral vector of the present invention, the virus is propagated in the host and collected. Generally, this involves collecting the cell supernatants at periodic intervals, and purifying the viral plaques from the crude lysate, using techniques well-known in the art, for example, cesium chloride density gradient. The titer (pfu/ml) of the virus is determined, and can be adjusted up (by filtration, for example), or down (by dilution with an appropriate buffer/medium), as needed. In the present invention, typical Ad titers are in the range of $10^{10}$–$10^{12}$ pfu/ml.

To effect the gene therapy aspect of the present invention, the isolated, purified viral vector-containing the neurotrophin-encoding nucleic acid is injected into a subject's lateral ventricles or ventricular zone wall under conditions effective to express the neurotrophic factor and to induce neuronal production in the subject. "Subject" is meant herein to include any member of the class Mammalia including, without limitation, humans and nonhuman primates, such as chimpanzees and other apes and monkey species; farm animals including cattle, sheep, pigs, goats and horses; domestic animals including cats and dogs; laboratory animals including rodents such as mice, rats, and guinea pigs, and the like. The term does not denote a particular age or sex. Thus, adults and post-natal (newborn) subjects, as well as fetuses, are intended to be covered.

The recombinant viruses of the present invention may be administered to a subject, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The recombinant viruses of this invention may be administered in sufficient amounts to transfect the desired cells and provide sufficient levels of integration and expression of the selected transgene to provide a therapeutic benefit without undue adverse effects or with medically acceptable physiological effects which can be determined by those skilled in the medical arts. While the preferable route of injection is the region of the lateral ventricle and ventricular wall zone of the subject's brain, other conventional and pharmaceutically acceptable parenteral routes of administration include direct delivery to the target organ, tissue or site, intranasal, intravenous, intramuscular, subcutaneous, intradermal, and oral administration are encompassed by the present invention.

Dosages of the recombinant virus will depend primarily on factors, such as the condition being treated, the selected gene, the age, weight, and health of the patient, and may thus vary among patients. A therapeutically effective human dosage of the viruses of the present invention is believed to be in the range of about 5 ml of saline solution containing concentrations of from about $2.5 \times 10^{10}$ pfu/ml to $2.5 \times 10^{12}$ pfu/ml virus of the present invention. Effective dosage for a given species can be determined by correcting for differences in surface area of the ventricular wall. The dosage will be adjusted to balance the therapeutic benefit against any side effects. The levels of expression of the selected gene can be monitored to determine the selection, adjustment, or frequency of dosage administration.

The present invention also relates to a method of recruiting new neurons to a subject's brain, including to regions of disease-related cell loss. This involves providing a nucleic acid construct encoding a neurotrophic factor and injecting the nucleic acid construct into the subject's lateral ventricles or ventricular zone wall under conditions effective to express the neurotrophic factor and to recruit neurons to the brain of the subject. Preparation of the DNA construct can be carried out as described above. Suitable nucleic acids include the neurotrophins given above, and viral propagation and injection are as described above. The present invention provides a method of recruiting neurons to the brain which is superior to those currently existing in the art and results in the recruitment of neurons to the olfactory bulb, the basal ganglia of the brain, the caudate nucleus, the putamen, and/or the globus pallidus, as well as to the to the cortex of a subject's brain.

Another aspect of the present invention relates to a method of treating a neurodegenerative condition. This involves providing a nucleic acid construct encoding a neurotrophic factor and injecting the nucleic acid construct into a subject's lateral ventricles or ventricular zone wall under conditions effective to treat a neurodegenerative condition, including, but not limited to, Huntington's Disease, Parkinson's Disease, amyotrophic lateral sclerosis (ALS; also known as Lou Gehrig's Disease), multiple sclerosis (MS), stroke, and traumatic injury to the brain and spinal cord. Preparation of the DNA construct can be carried out as described above. Nucleic acids suitable for this method include the neurotrophins listed above, and viral propagation and injection are carried out as described above.

Huntington's Disease (HD) is an autosomal dominant neurodegenerative disease characterized by a relentlessly progressive movement disorder with devastating psychiatric and cognitive deterioration. HD is associated with a consistent and severe atrophy of the neostriatum which is related to a marked loss of the GABAergic medium-sized spiny projection neurons, the major output neurons of the striatum. The intraventricular injections of BDNF DNA in a viral vector results in a distinct population of newly generated neurons in the neostriatum, indicating that the neurotrophic factor BDNF is particularly useful as a potential treatment for HD. Direct injection of BDNF also would be useful in treating Huntington's Disease.

Another aspect of the present invention relates to a method of treating a neurological condition by providing the neurotrophic factor BDNF and injecting that factor into a subject's lateral ventricles or ventricular zone wall under conditions effective to treat the neurodegenerative condition. In this aspect of the present invention, the BDNF may be a recombinant protein (i.e., an expression product of a BDNF-DNA construct). The protein in either form can be isolated by conventional means, such as column purification or purification using an anti-protein antibody.

In all aspects of the present invention, the injection of a neurotrophic factor encoding nucleic acid into the subependyma, the cellular layer lining the ventricular cavities of the adult brain, is intended to activate and mobilize endogenous neuroprogenitor cells of the diseased or injured brain and spinal cord in order to restore lost brain cells. The resulting production of new neurons and the recruitment of new neurons to regions of the brain, such as the striatum and the cortex, suggest that neuronal populations may be replaceable in the brain and spinal cord of subjects suffering from neurodegenerative diseases including, but not limited to, Huntington's Disease, Parkinson's Disease, amyotrophic lateral sclerosis, and multiple sclerosis, as well as in victims of neurological damage due to stroke or traumatic injury to the brain and/or spinal cord.

EXAMPLES

Example 1

Adenovirus Construction

An adenoviral vector was constructed bearing BDNF under the control of the constitutive CMV promoter, placed in tandem sequence with green fluorescent protein (hGFP), under the control of an internal ribosomal entry site (IRES) (Morgan, R. et al, "Retroviral Vectors Containing Putative Internal Ribosomal Entry Sites: Development of a Polycistronic Gene Transfer System and Applications to Human Gene Therapy," *Nucleic Acids Res.* 20:1293–1299 (1992), which is hereby incorporated by reference in its entirety). In brief, BDNF cDNA (Regeneron Pharm., Tarrytown, N.Y.) was obtained in SpeI/HindIII. A HindIII/SalI segment containing an IRES site (Morgan, R. et al, "Retroviral Vectors Containing Putative Internal Ribosomal Entry Sites: Development of a Polycistronic Gene Transfer System and Applications to Human Gene Therapy," *Nucleic Acids Res.* 20:1293–1299 (1992), which is hereby incorporated by reference in its entirety), and hGFP were taken from pTRUFIII (Levy, J. et al, "Retroviral Transfer and Expression of a Humanized, Red-shifted Green Fluorescent Protein Gene into Human Tumor Cells," *Nature Biotech.* 14:610–614 (1996), which is hereby incorporated by reference in its entirety). On digestion with SpeI-HindIII of pBDNF, the 1.1 kb TRUFIII HindIII-SalI fragment was ligated into the adenovirus shuttle vector pCMV:SV2, and digested with SpeI/SalI. The resultant construct was designated pAdP/CMV:BDNF:IRES:hGFP. Established methods (Graham et al., "Manipulation of Adenovirus Vectors," In *Methods in Molecular Biology*, E. Murray, ed.: Humana, pp. 109–128 (1991), which is hereby incorporated by reference in its entirety) were then used to construct a replication-defective recombinant adenovirus, via homologous recombination using the plasmid pJM17, which contains the E1A-deleted type 5 adenovirus. pAd5-CMV:BDNF:IRES:hGFP was co-transfected with pJM17 into HEK293 cells, and viral plaques developed for 2 weeks. Crude viral lysates were then used for plaque purification. Virus was propagated in HEK293 cells, purified by cesium chloride density gradient centrifugation, and stored at −70° C. The resultant titer of AdBDNF was between $10^{11-1012}$ pfu/ml; however, both AdBDNF and its AdNull (AdCMV:hGFP) control were titered to $2.5 \times 10^{10}$ pfu/ml before use, to ensure that experimental and control rats received equivalent viral loads (see below). The efficacy of AdBDNF in driving expression of BDNF was verified in HeLa cells by ELISA. In addition, the expression of GFP by each virus was confirmed in sections of the adult ventricular wall of injected rats, by direct fluorescence observation, as well as by in situ hybridization of both BDNF and GFP.

Example 2

Cell Culture and In Vitro Experiments

HeLa cells were plated at a density of $1 \times 10^6/25$ cm² in Ham's F12 with 10% FBS. After 24 hours, the cells were infected with 1, 10, or 100 moi (multiplicity of infection) of AdBDNF or AdCMV:GFP, in F12 with 1% FBS. After 24 hours, serum was added to achieve a 10% concentration of FBS. After another 24 hours, the cells were washed and switched to serum-free media for three days. The cells and their media were then separately collected; the media was decanted to storage at −80° C., for later ELISA of BDNF, while the cells were collected in Ca/Mg-free HBSS/1 mM EDTA and pelleted. The cellular pellet was then resuspended in 10% FBS-containing media, and subjected to a viability assay; this was done to assess potential viral toxicity in these same cultures. Triplicate 50 µl aliquots of resuspended cells were diluted in trypan blue (1:1) to label dead cells; both live and dead cells were separately counted 20 minutes later by hemocytometer and their ratio determined.

Example 3

Experimental Design and Stereotactic Injection

Either the Ad5CMV:BDNF:IRES:hGFP (AdBDNF) or AdCMV:hGFP (AdNull) viruses were delivered as single 3 µl injections into the lateral ventricles of 7 adult rats. Both viruses were established in the same backbone and titered to $2.5 \times 10^{10}$ pfu/ml before use. Using a Kopf stereotactic frame, the rats were injected at the following coordinates: AP −0.3 mm, ML ±1.2 mm, DV −3.6 mm (Paxinos). The rats were injected intraperitoneally (IP) daily for 18 d thereafter with the mitotic marker bromodeoxyuridine (BrdU), 100 mg/kg. Control animals were injected with either AdCMV:GFP (AdNull; n=5) or PBS (n=5). These animals were sacrificed on the day following the last BrdU injection (day 20). Among them, 4 each of the AdBDNF, AdNull-and PBS-injected animals were used for the quantification of BrdU+ cells in the olfactory bulb, striatum, and other regions assessed; the remainder of the animals sacrificed on day 20 were used to supplement our assessment of the CSF BDNF levels.

An additional sample of 3 rats was injected with AdBDNF and BrdU as noted, but sacrificed on the 35th day after the completion of BrdU treatment, on day 56 following viral injection. These rat brains were examined solely with regards to the persistence of BrdU+ neurons in the neostriatum. In all groups, daily weights were recorded beginning with the day of viral injection, through the day of sacrifice.

Example 4

ELISA Assay of CSF and Cell Supernatants

At 20 days after viral injection, rats were injected with 0.6 ml of 65 mg/ml pentobarbital, and perfused with Hank's Balanced Salt Solution with $Mg^{2+}/Ca^{2+}$ (Gibco-BRL, Bethesda, Md.). Cerebral spinal fluid (CSF) was collected from the cisterna magna, aliquoted, and stored at −80° C. The BDNF in the CSF of both PBS-injected and AdNull or AdBDNF-injected rats was quantified using a two-site ELISA (Emax Immunoassay System, Promega, Madison, Wis.) (Mizisin, A. et al, "BDNF Attenuates Functional and Structural Disorders in Nerves of Galactose-fed Rats," *J. Neuropathol. Exp. Neurol.* 56:1290–1301 (1997), and Leventhal, C. et al, "Endothelial Trophic Support of Neuronal Production and Recruitment by the Adult Mammalian Subependyma," *Molec. Cell. Neurosci.* 13:450–464 (1999), which are hereby incorporated by reference in their entirety). Briefly, the monoclonal anti-BDNF capture antibody did not cross react with other members of the neurotrophin family at concentrations up to 10,000 times that used for the standard curve, while the reporter antibody was a biotinylated rabbit polyclonal anti-BDNF, similarly selective for BDNF. The dynamic range of the ELISA was 10 pg/ml-20 ng/ml for undiluted samples; all samples were diluted in assay buffer to bring them into the linear range of the assay's standard curve. The CSF BDNF determinations were derived from 7 AdBDNF-, 5 AdNull-, and 3 PBS-injected animals. Total protein levels of each CSF sample were assessed by BCA assay (Pierce Chemical Co., Rockford, Ill.).

Cells for the supernatants of AdBDNF- and AdNull-infected HeLa cell layers, BDNF levels were reported as the average of triplicate samples.

Example 5

In Situ Hybridization

BDNF antisense and sense probes were generated from pSK-rBDNF, (Regeneron Pharmaceuticals, Tarrytown, N.Y.). The BDNF plasmid DNA was linearized with either BamHI for the anti-sense probe or EcoRV for the sense control, then transcribed in vitro using either T7 RNA polymerase for the anti-sense probe, or T3 RNA polymerase for the sense probe. The antisense GFP probe was generated by linearizing pGFP with XbaI, and transcribing in vitro with T3 RNA polymerase. The probes were non-isotopically labeled with digoxigenin-11-UTP (Boehringer Mannheim-Roche Diagnostics, Indianapolis, Ind.).

A series of 15 µm cryostat sections were permeabilized with 0.3% Triton X-100 in PBS for 15 min. The sections were dehydrated in ascending alcohols, cleared with xylene, rehydrated, and treated with Proteinase K (1 µg/ml) for 30 min at 37° C., and postfixed with 4% paraformaldehyde for 5 min. To acetylate sections, slides were incubated for 30 min in 0.1M triethanolamine (TEA) buffer, pH 8.0, containing 0.25% acetic anhydride. The sections were prehybridized with 4×SSC containing 50% formamide for 1 hr, then hybridized under coverslips for 15 h at 42° C. with digoxygenin-labeled sense or anti-sense probes (300 ng/ml) in 40% deionized formrnamide, 10% dextran sulfate, 1×Denhardt's, 4×SSC, 10 mM dithiothreitol, and 1 mg/ml salmon sperm DNA. After hybridization, the sections were washed in 2×SSC for 5 min to remove the coverslips, washed with 50% formamide in 2×SSC for 20 min at 52° C., washed in 2×SSC, and treated with RNase A (20 µg/ml) in 2×SSC for 30 min at 37° C. After 4 washes in 2×SSC, the sections were washed with 0.2×SSC at 55° C. for 1 hr.

For detection of digoxygenin-labeled probes the slides were washed in Tris buffered-saline (TBS: 0.1M TrisHCl with 150 mM NaCl), 3×5 min, blocked in 0.1% Triton X-100 and 2% sheep serum for 30 min, and incubated overnight at 4° C. in AP-conjugated anti-digoxygenin (1:100, Boehringer Mannheim). After washing with TBS, the sections were switched to detection buffer (100 mM Tris-HCl, pH 9.5, with 100 mM NaCl, 50 mM MgCl2) for 10 min, and incubated in NBT-BCIP solution (Bio-Rad Labs, Hercules, Calif.) with 1 mM levamisole for 2–20 hrs in the dark. Upon color development, the reaction was terminated by washing (3×5 min) in TBS with 10 mM EDTA.

Example 6

Immunohistochemistry

The animals were sacrificed, perfusion fixed and their brains removed on either the 20th or 56th day after viral injection. Fixation was accomplished using 4% paraformaldehyde in 0.1M phosphate buffer (PB; pH 7.4), with a 90 min post-fix followed by immersion and sinking in 30% sucrose in PB. All brains were cut as 15 µm sagittal sections that included the olfactory bulb and rostral migratory stream rostrally. These sections were stained for BrdU, using immunoperoxidase detection when staining for BrdU alone, or double-immunofluorescence when staining for both BrdU and neuronal markers. Individual sections were denatured in 2N HCl for an hour, then stained for BrdU, using rat anti-BrdU antibody at 1:200 (Harlan Bioproducts, Indianapolis, Ind.), followed serially by fluorescein-conjugated anti-rat IgG at 1:150 (Jackson Labs, Bar Harbor, Me.). The sections were then washed and stained for either β-III-tubulin, using the TuJ1 monoclonal antibody (Lee, M. et al., "Posttranslational Modification of Class III b-tubulin," *Proc. Nat'l. Acad. Sci. USA* 87:7195–7199 (1990), which is hereby incorporated by reference in its entirety); MAP-2, using rabbit anti-MAP2 (Bernhardt, R. et al., "Light and Electron Microscopic Studies of the Distribution of Microtubule-Associated Protein 2 in Rat Brain: A Difference Between Dendritic and Axonal Cytoskeletons," *J. Comp. Neurol.* 226:203–21 (1984), which is hereby incorporated by reference in its entirety); NeuN (Chemicon, Temecula, Calif.) (Eriksson, P. et al., "Neurogenesis in the Adult Human Hippocampus," *Nature Medicine* 4:1313–1317 (1998), which is hereby incorporated by reference in its entirety); GAD67 (Sigma, St. Louis, Mo.); calbindin-D28K (Guan, J et al., "Selective Neuroprotective Effects with IGF-1 in Phenotypic Striatal Neurons Following Ischemic Brain Injury in Fetal Sheep," *Neuroscience* 95:831–839 (1999), which is hereby incorporated by reference in its entirety) (Sigma, St. Louis, Mo.); or DARPP-32 (Ivkovic, S. et al, "Expression of the Striatal DARPP-32/ARPP-21 Phenotype in GABAergic Neurons Requires Neurotrophins in Vivo and In Vitro," *J. Neurosci.* 19:5409–5419 (1999), which is hereby incorporated by reference in its entirety), each as previously described (Eriksson, P. et al., "Neurogenesis in the Adult Human Hippocampus," *Nature Medicine* 4:1313–1317 (1998); Goldman, S. A. et al., "In Vitro Neurogenesis by Neuronal Precursor Cells Derived from the Adult Songbird Brain," *J. Neuroscience* 12:2532–41 (1992); Guan, J et al., "Selective Neuroprotective Effects with IGF-1 in Phenotypic Striatal Neurons Following Ischemic Brain Injury in Fetal Sheep," *Neuroscience* 95:831–839 (1999); Ivkovic, S. et al, "Expression of the Striatal DARPP-32/ARPP-21 Phenotype in GABAergic Neurons Requires Neurotrophins in Vivo and In Vitro," *J. Neurosci.* 19:5409–5419 (1999); Menezes, J. R. et al, "Expression of Neuron-specific Tubulin Defines a Novel Population in the Proliferative Layers of the Developing Telencephalon," *J Neurosci.* 14:5399–416 (1994); Roy, N. et al, "In Vitro Neurogenesis by Neural Progenitor Cells Isolated from the Adult Human Hippocampus," *Nature Medicine* 6:271–277 (2000), which are hereby incorporated by reference in their entirety). All anti-mouse secondary antibodies were pre-absorbed against rat IgG to avoid nonspecific staining.

Example 7

Confocal Imaging

In sections double-stained for BrdU together for either β-III-tubulin, MAP-2, NeuN, DARPP-32, GAD67 or calbindin-D28, single BrdU+ cells that appeared to be double-labeled for both the neuronal antigen and BrdU were further evaluated by confocal imaging. Using a Zeiss LSM510 confocal microscope, images were acquired in both red and green emission channels using an argon-krypton laser. The images were then viewed as stacked z-dimension images, both as series of single 0.9 µm optical sections, and as merged images thereof. The z-dimension reconstructions were all observed in profile, as every BrdU+ cell double-labeled with a neuronal marker was then observed orthogonally in both the vertical and horizontal planes. Only after 3 observers independently deemed individual cells as double-labeled, with central BrdU immunoreactivity surrounded by neuronal immunoreactivity at all observation angles, in every serial optical section, and in each merged and rotated composite, were the cells scored as double-labeled, newly-generated neurons.

Example 8

Scoring and Quantification

Unbiased counting was used to score the number, density, and distribution of BrdU+ cells in the injected brains, using an optical dissector procedure (Kuhn, H. G. et al, "Epidermal Growth Factor and Fibroblast Growth Factor-2 Have Different Effects on Neural Progenitors in the Adult Rat Brain," *J. Neuroscience* 17:5820–5829 (1997); Sterio, D., "The Unbiased Estimation of Number and Sizes of Arbitrary Particles Using the Dissector," *J. Microsc.* 134:127–136 (1984); West, M., "Stereological Methods for Estimating the Total Number of Neurons and Synapses: Issues of Precision and Bias," Trends in Neurosci. 22:51–61 (1998), which are hereby incorporated by reference in their entirety). To estimate the number of BrdU-labeled cells per region, 22 15 µm sections/animal were sampled, for both experimental and control brains; for each, every sixth section was analyzed, at 90 µm intervals. The first section of each sagittal series was chosen randomly, from a total sample that was accumulated beginning with the first appearance of the olfactory cortex on cresyl violet stained alternate sections. Typically, the sampled region included that subtended by the stereotactic coordinates L0.3–2.3 bilaterally. By this means, a 2 mm mediolateral segment in the sagittal plane, centered on the RMS, was sampled.

The absolute number of total BrdU+ cells in every eighth 15 µm sagittal section was counted in each of 6 regions: 1) the anterior surface of the ventricular zone (VZ), 2) the olfactory subependyma of the rostral migratory stream (RMS), 3) the olfactory bulb, 4) the medial septum, 5) the neostriatum, and 6) the frontal cortex overlying the corpus callosum, rostral to the perpendicular extension of the rostral-most wall of the lateral ventricle.

In each sampled section, every BrdU+ nucleus was counted in each scored region; the positions of each of these cells were entered manually into BioQuant image analysis software with its incorporated topography reconstruction package, and the results tabulated. For each region, the results were reported as the mean number of BrdU+ cells/section. In addition, for the olfactory bulb and the neostriatum, these counts were converted into BrdU+ cells/mm$^3$ after determining the surface areas and hence volumes of each scored region (Michel, R. et al, "Application of the Cavalieri Principle and Vertical Sections Method to Lung: Estimation of Volume and Pleural Surface Area," *J. Microsc.* 150:117–136 (1988), which is hereby incorporated by reference in its entirety). Statistical analysis was then accomplished by analysis of variance (ANOVA) followed by post-hoc Boneferroni t-tests.

To estimate total striatal neuronal number, the number of striatal neurons were counted in each of 6 age and sex-matched rats, 3 of which were treated with AdBDNF and the other 3 with AdNull as a negative control (n=3). From each, eight 15 µm sections were analyzed, representing every 32nd sequentially, thereby sampling at 480 µm intervals beginning with the first appearance of rostrocaudally-oriented striatal fascicles on cresyl violet stained alternate sections. In these cresyl violet-stained sections, the number of neurons in each striatum were counted under high magnification using morphological criteria for neuronal identity, by an observer blind with regard to the experimental group. To this end, neurons were defined as large cells of >10 µm diameter, with pale central nuclei and central nucleoli, in an otherwise basophilic cytoplasm. To ensure the validity of these criteria, 2 sections from each set of 8 were destained by acidified ethanol, then immunostained for calbindin. The number of calbindin-defined striatal neurons was then counted and compared to that obtained in the same section by cresyl violet. A >98% concordance was found in the neuronal counts obtained using these 2 methods.

Example 9

Figure 1C:
Figure 1A:
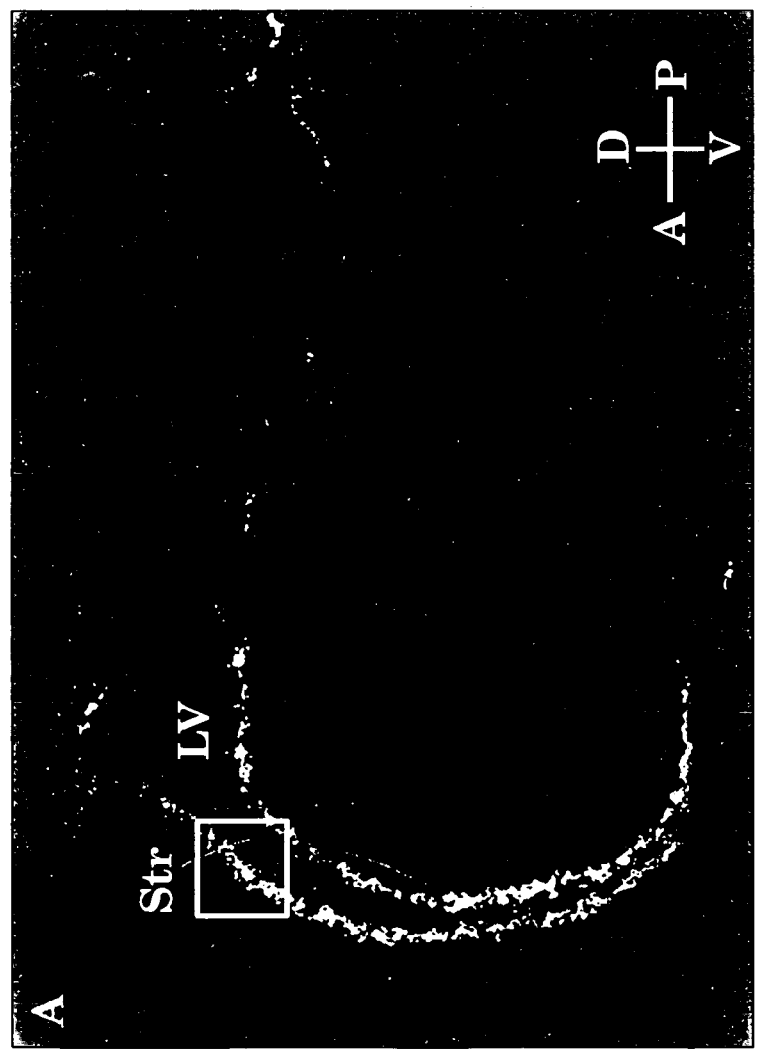

Intraventricular Delivery of Adenoviral CMV:hGFP Restricted Transgene Expression to the Adult Ependyma and Subependyma To first assess the distribution of adenoviral transduction following a single intraventricular injection of virus, adenovirus bearing the gene encoding green fluorescent protein (hGFP), placed under the control of the CMV promoter, was injected into the lateral ventricles of 4 adult Sprague-Dawley rats. The rats were sacrificed either 1 or 3 weeks later, and their brains prepared for histology. As shown in FIG. 1, it was found that in all 4 rats, most ependymal and scattered subependymal cells labeled heavily to single viral injection, with virtually the entire lining of the lateral ventricle noted to express GFP after injection of $3 \times 10^7$ pfu adenovirus (3 µl of $10^{10}$ pfu/ml). Little parenchymal expression of GFP was noted, despite the lack of specificity of the CMV promoter, suggesting that viral penetration outside of the subependyma was minimal The restriction of transgene expression to the ventricular wall suggested that ependymal cells might be targeted selectively on spatial grounds alone, even without benefit of cell-specific promoters.

Example 10

AdBDNF-Infected Cells Expressed BDNF In Vitro

Figure 2A:
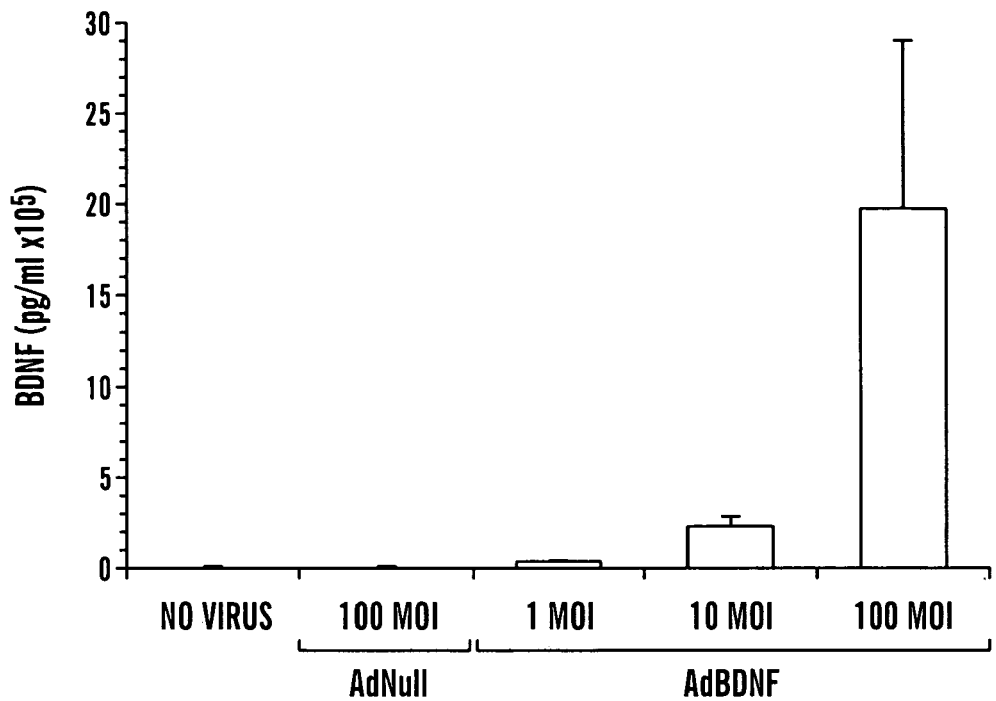
FIGS. 2A–D show adenoviral BDNF infection yielded high level BDNF expression in vitro and in vivo.
Figure 2B:
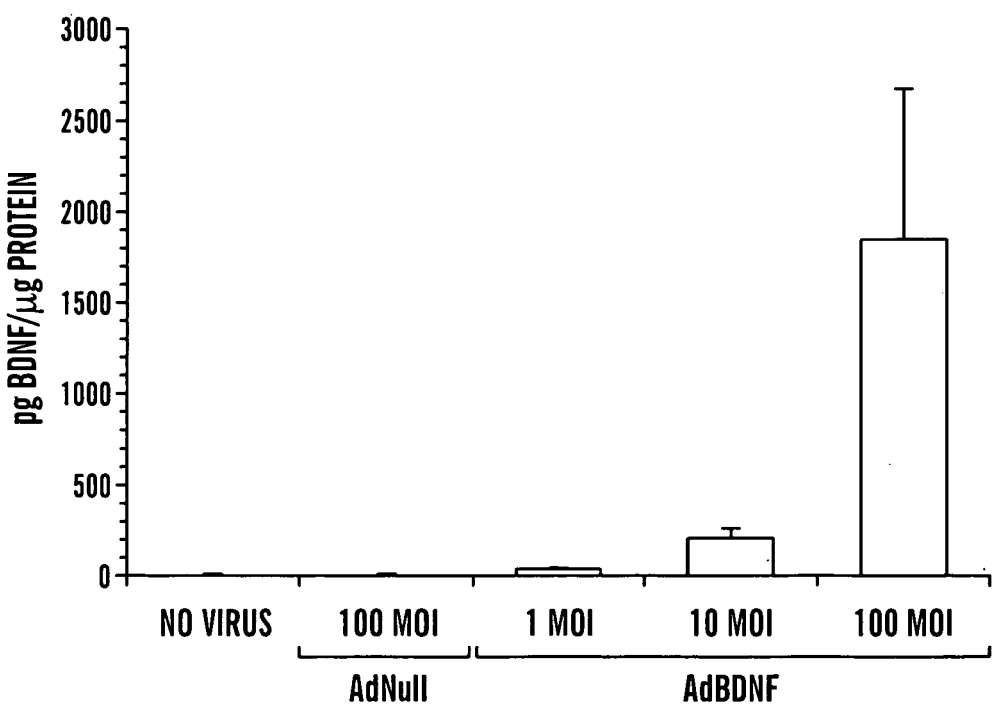

The effects of adenovirally-delivered BDNF on the adult ventricular zone pool were assessed as follows. A ΔE1 type 5 adenovirus was thus constructed to express BDNF, under the control of the constitutively activated CMV promoter; the virus also included hGFP as a reporter, placed under IRES promoter control. The resultant vector, AdCMV:BDNF:IRES:hGFP (hereafter referred to as AdBDNF) was characterized first by infecting HeLa cells, which typically do not express BDNF. The production of BDNF by the infected HeLa cells was assessed as a function of time after infection, using ELISA of BDNF secreted into the culture media. BDNF release in response to AdBDNF-infection was compared to that of both untransfected and AdCMV:hGFP (AdNull)-infected control cells, as shown in FIGS. 2A–B. Within 2 days after infection with 10 pfu/cell AdBDNF, 234±54.5 ng/ml of BDNF protein were measured in the culture supernatant, roughly 250-fold the levels observed in the uninfected (0.8±195 1.0 ng/ml) and AdNull-infected (1.0±0.6 ng/ml) control cultures. Thus, AdBDNF directed high-level expression of BDNF by HeLa cells.

To ensure that transgene expression was not accomplished at the expense of cell viability, trypan blue inclusion was assessed as a function of viral dose over the range 1–10 moi/cell. Results of the trypan blue exclusion tests showed that adenovirus-associated toxicity was minimal, and statistically insignificant over this dose range. In addition, to ensure that this dose range was no more toxic for primary brain cells than for HeLa cells, the effect of increasing viral dose on the viability of primary adult human astrocytes, obtained from temporal lobes resected from adult epileptic patients (see Leventhal, C. et al, "Endothelial Trophic Support of Neuronal Production and Recruitment by the Adult Mammalian Subependyma," *Molec. Cell. Neurosci* 13:450–464 (1999), which is hereby incorporated by reference in its entirety) was also determined. It was found that astrocytes exposed to 10 moi AdBDNF exhibited no significant increment in lethal toxicity at 48 hrs after infection.

Example 11

CSF Levels of BDNF Rose Markedly Following Intraventricular Injection of AdBDNF

Figure 2C:
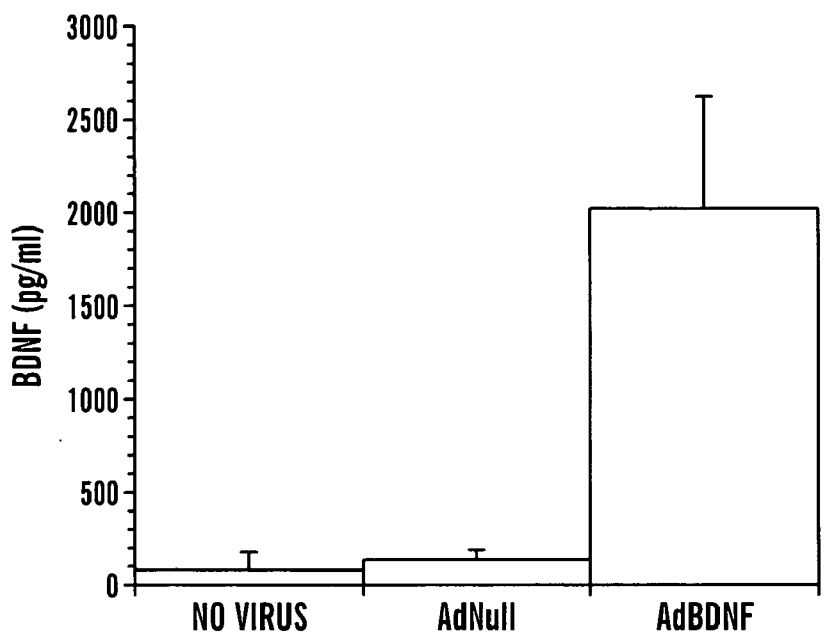
Figure 2D:
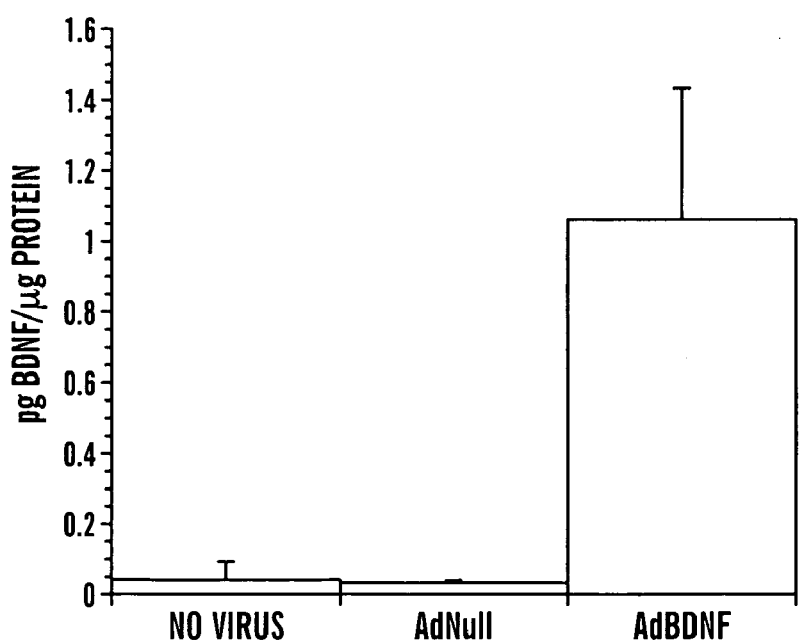

To assess the level of release of BDNF protein into the CSF of AdBDNF-treated rats, a total of 14 animals were injected with either AdBDNF (n=7), AdNull (n=5), or PBS (n=2); all were subjected to cisterna magna puncture for CSF withdrawal at 3 weeks after viral infection. In the AdBDNF-injected animals, ELISAs revealed that CSF BDNF levels averaged 1.07±0.3 µg/g protein (mean±SE), when assessed 3 weeks after injection, as shown in FIGS. 2C–D. This represented 2.02±0.6 ng BDNF/ml of ventricular CSF, a level at the lower end of the dose range (2–40 ng/ml) appropriate for eliciting trkB-mediated biological effects in vitro (Lindsay, R. M. et al, "Neurotrophic Factors: From Molecule to Man," *Trends in Neurosciences* 17:182–90 (1994), which is hereby incorporated by reference in its entirety). In contrast, BDNF was undetectable in both the PBS and AdCMV:GFP controls (p=0.025 by ANOVA [F=5.24; 2, 13 d.f.]). The absence of detectable BDNF in the AdNull-injected controls indicated that the BDNF levels achieved in the CSF of AdBDNF-treated animals was a product of the virally-encoded BDNF transgene. Thus, adenoviral transduction of the adult ventricular ependyma permitted high-level delivery of BDNF to the brain and CSF, with expression that was sustained for at least 3 weeks after viral infection.

Example 12

Adenoviral-Transduced BDNF mRNA Restricted to Ventricular Wall

Figures 3D, 3E:
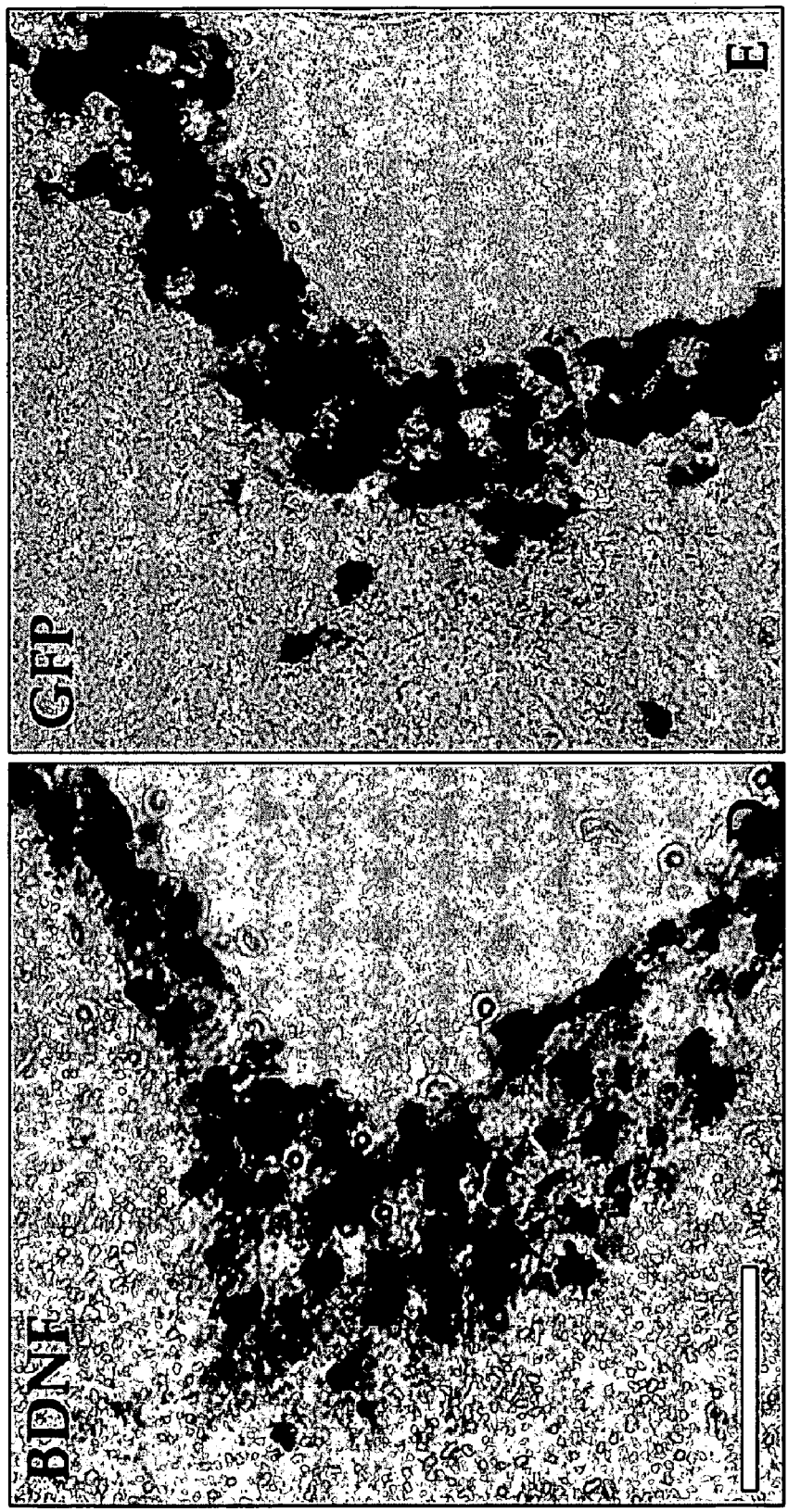

In situ hybridization, using RNA probes for BDNF and hGFP, revealed that AdCMV: BDNF:IRES:GFP transduced expression of both BDNF and hGFP mRNA in vivo. Strikingly, BDNF and GFP mRNAs were largely restricted to the wall of the lateral ventricular system, as shown in FIG. 3. Even when assessed 3 weeks after viral injection, cells overexpressing BDNF and GFP were largely limited to the ventricular wall, with little or no infiltration of the rostral migratory stream or bulb. Thus, at least rostrally along the anterior face of the ventricle, the infected cell pool appeared to be ependymal, with little or no direct infection of subependymal neuronal migrants. This pattern appeared to be maintained along most of the rostrocaudal extent of the ventricular system, throughout which virally-transduced BDNF and GFP mRNAs were limited to the ependymal surface, except at the rostral tip of the lateral ventricles, where scattered subependymal labeling was also noted.

Example 13

Figure 4A:
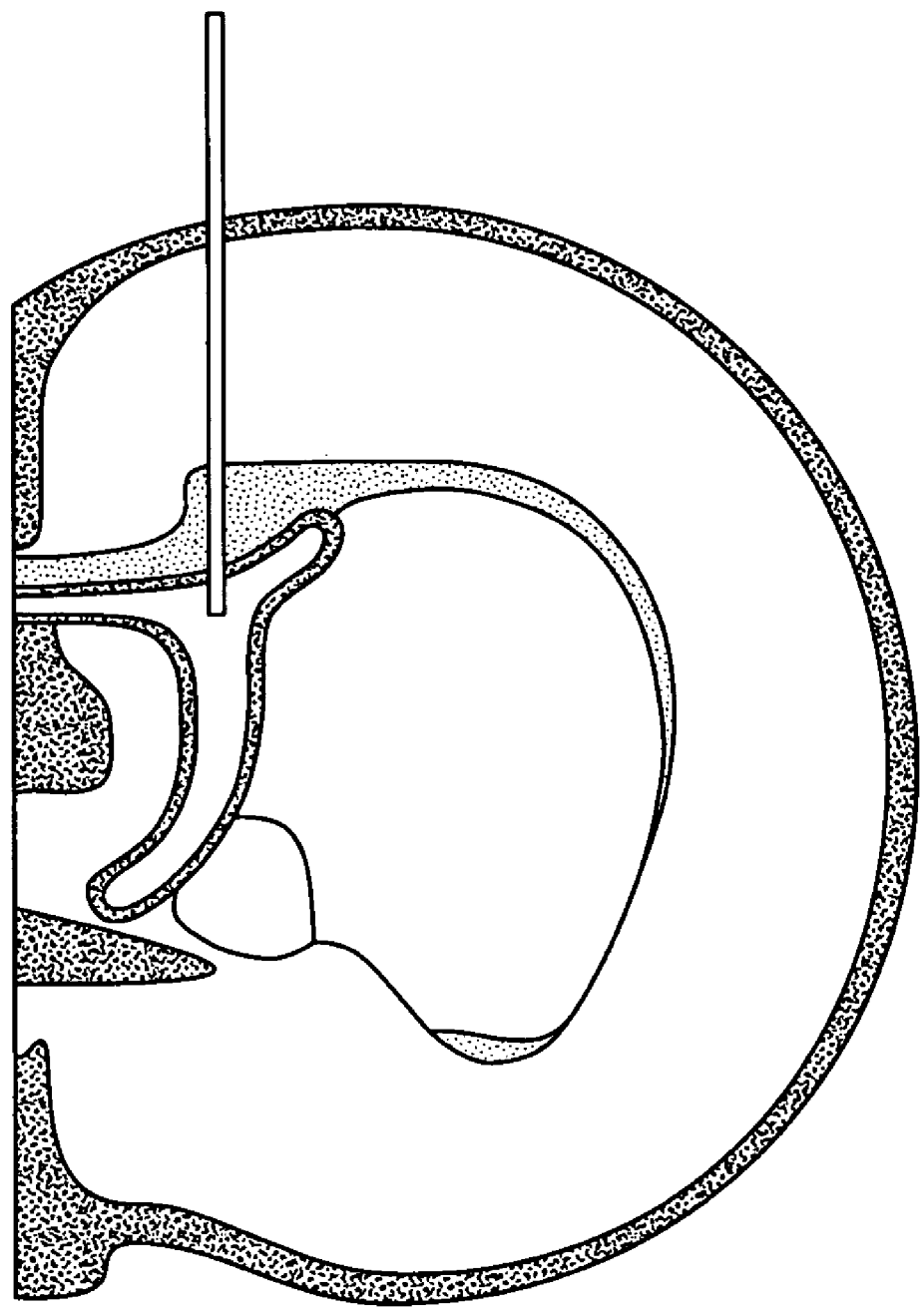
FIG. 4A is a schematic coronal section showing the site of injection of adenovirus into the lateral ventricle.
Figure 4B:
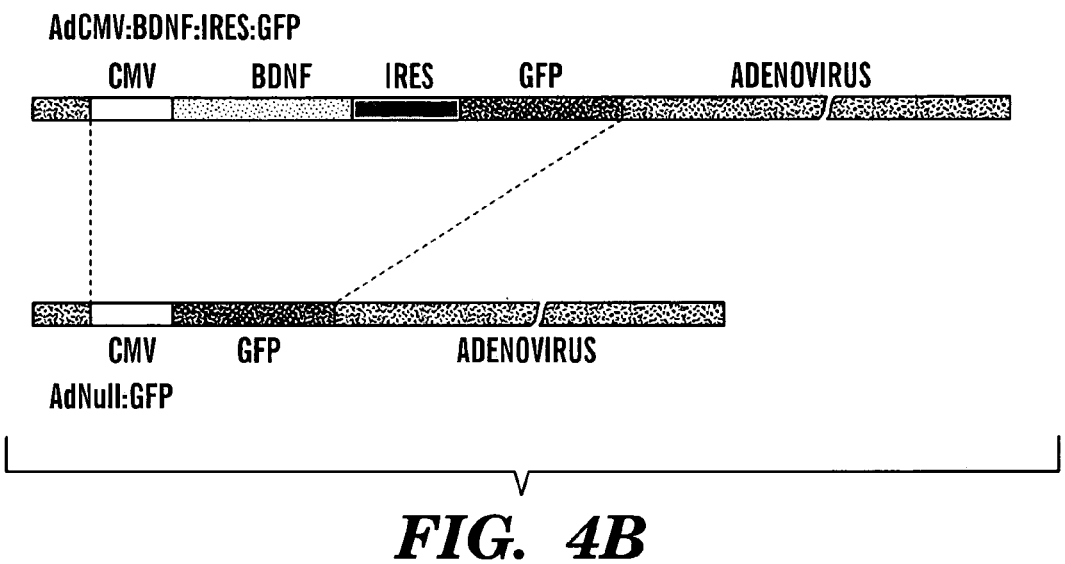
FIG. 4B shows vector E1-deleted (ΔE1) adenoviral type 5 constructs used to express a dicistronic transcript of BDNF and hGFP (or hGFP alone, as a control vector) under the control of the constitutive CMV early promoter.
Figure 4C:
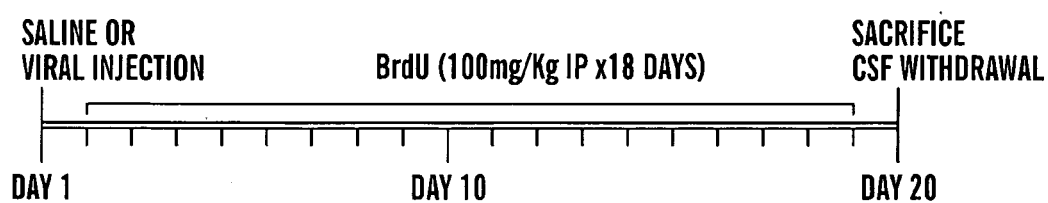
FIG. 4C depicts an experimental protocol where adenovirus was injected on day 1, followed by IP injections of 100 mg/kg BrdU for the next 18 days. On day 20, cerebral spinal fluid (CSF) was extracted for BDNF ELISA, and the brains were processed for BrdU immunohistochemistry in tandem with phenotype-specific immunolabeling.

AdBDNF Infection of the Ventricular Wall Increased Substantially the Number of New Neurons in Both the Rostral Migratory Stream and Olfactory Bulb To follow the generation and fates of new neurons generated from the AdBDNF-treated ventricular zone, an initial cohort of rats were injected with either AdBDNF or AdNull (n=4/group). These injections were followed with daily intraperitoneal injections of BrdU, at 100 mg/kg for the next 18 days. On day 20, the animals were sacrificed, CSF was extracted for BDNF ELISA, and the brains fixed along with the olfactory bulbs. The brains were then sectioned and stained for BrdU in tandem with phenotype-specific markers. This strategy is detailed in FIGS. 4A–C.

Figure 5E:
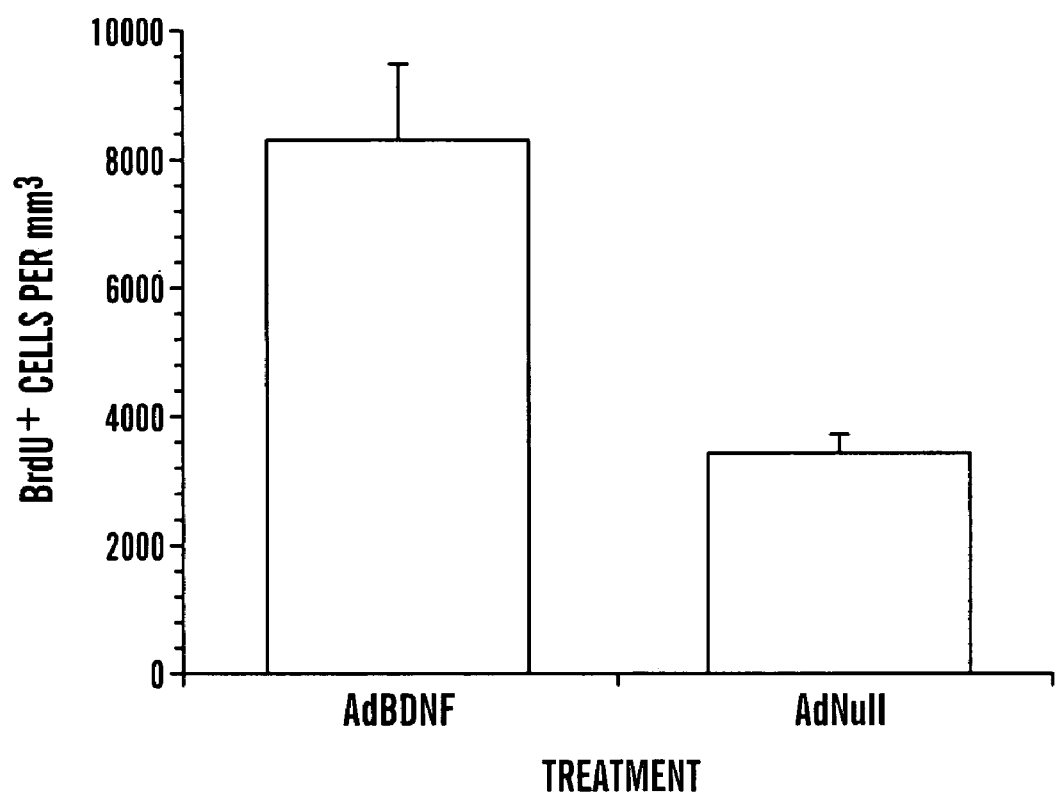

The effects of AdBDNF on neuronal recruitment were first assessed in the region of the rostral migratory stream, as measured posteriorly from the striatum and its ventricular wall up to, and including, the internal granular layer of the olfactory bulb. Within this region, the incidence of BrdU+ cells rose from 3398±346 cells/mm$^3$ (±SE) in the control animals to 8288±1199 cells/mm$^3$ in the AdBDNF-treated rats. FIGS. 5A and 5B show the presence of BrdU+ cells in AdBDNF-treated brains and control brains, respectively. Within the olfactory bulb itself (measured rostrally from the line connecting the dorsal and ventral posterior borders of the olfactory cortex), AdBDNF treatment increased by 2.44±0.1-fold the number of BrdU+ cells, relative to the AdNull controls (p=0.0006 by ANOVA [F=42.1; 1, 7 d.f.]), as seen in FIGS. 5C–D. This value reflected the cell counts obtained from scoring entire sagittal sections of the olfactory bulb. The values included both the internal and external granular zones of the scored bulbs. As shown in FIG. 5E, the number of cells migrating to the olfactory bulb was substantially greater in the AdBDNF-treated animals than their AdNull controls.

In both the AdBDNF and AdNull animals, the BrdU+ cells were double-immunostained for β-III-tubulin and/or MAP-2, to establish the proportion of neurons within the total BrdU+ cell pool. In both groups, BrdU-incorporating cells found within the olfactory stream almost invariably expressed β-III-tubulin-immunoreactivity, as shown in FIG. 6. The same was true in the olfactory bulb, within which double-labeled cells for MAP-2/BrdU were also frequent. Interestingly, MAP-2-labeled BrdU+ cells were seen only in the olfactory bulb, and not in the olfactory subependyma or migratory stream. Instead, these cells were first noted within the granular layer of the olfactory bulb itself, consistent with the differentiation of mitotic β-III-tubulin+ neuroblasts to postmitotic MAP-2+ neurons upon terminal migration from the olfactory subependyma to the olfactory cortex (Goldman, S. A. et al., "Strategies Utilized by Migrating Neurons of the Postnatal Vertebrate Forebrain," *Trends in Neurosciences* 21:107–114 (1998); Lois, C. et al, "Chain Migration of Neuronal Precursors," *Science* 271:978–981 (1996), which are hereby incorporated by reference in their entirety). Quantitatively, in the AdNull-treated rats, 93.2±0.5% of BrdU+ cells in the olfactory bulb expressed β-III-tubulin. This proportion was virtually identical to that obtained in the AdBDNF-treated olfactory bulbs, in which an average of 93.0±1.8 and 89.4±2.4% of BrdU+ cells co-expressed neuronal β-III-tubulin or MAP-2, respectively. These data indicate that most cells recruited to the olfactory bulbs were neurons, and that AdBDNF substantially promoted the addition of these new neurons to the adult olfactory system.

Example 14

Confocal Imaging Confirmed Cells Added to the Olfactory Bulbs Were Neurons

High-magnification confocal imaging confirmed the neuronal antigenicity of the BrdU-labeled cells in both the rostral migratory stream and olfactory bulb. Representative sections were taken from 4 brains, including 2 AdBDNF-treated experimental animals and 2 AdNull control animals. Mid-sagittal sections derived from each of these were double-immunostained for BrdU together with either β-III-tubulin or MAP-2, and imaged via confocal laser scanning, with compositing and reconstruction in the z-dimension to ensure the neuronal immunoreactivity of BrdU+ cells. This confirmed that those BrdU+ cells added to the olfactory bulb were almost entirely neurons, in that they expressed MAP-2 as well as β-III-tubulin, and did so in both the AdBDNF and AdNull-treated animals. As shown in FIG. 6, merged z-stacks of confocal images of MAP-2+ and β-III tubulin+ neurons, co-labeled for BrdU, confirmed that >90% all BrdU+ nuclei in the olfactory bulb were harbored by MAP-2+ or β-III tubulin+ cells. This indicated that the AdBDNF-associated increases in the olfactory bulb BrdU labeling indices reflected enhanced neurogenesis and/or recruitment in the treated animals.

Example 15

Ventricular AdBDNF Infection Induced Striatal Neuronal Recruitment

Figure 7:
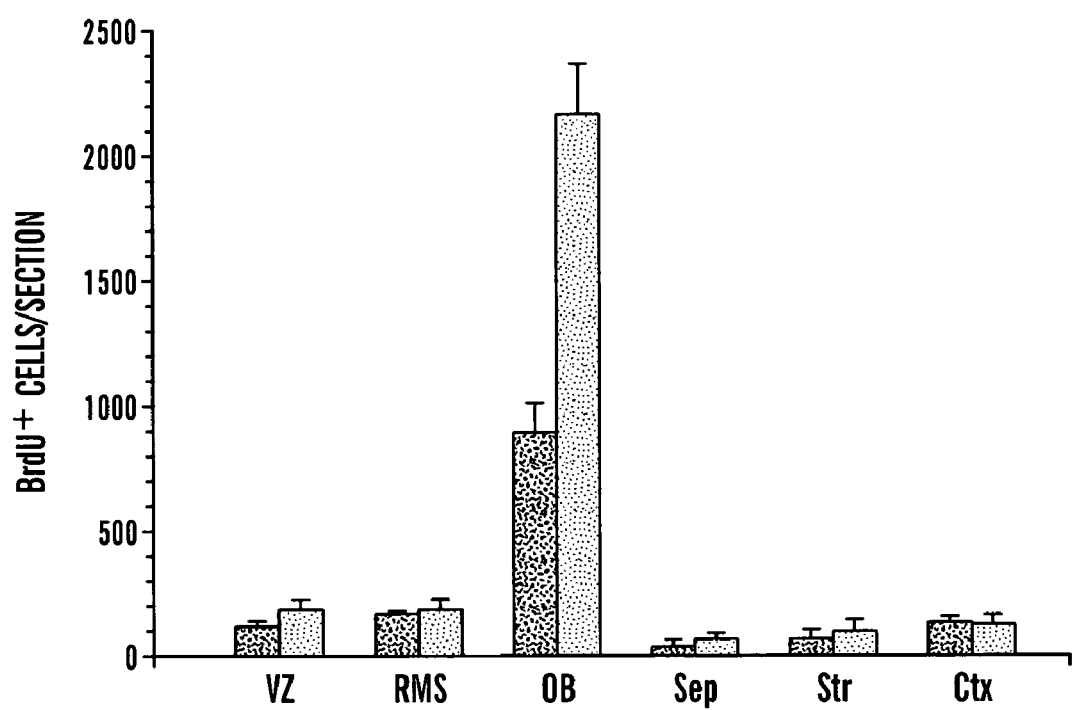
FIG. 7 shows that the difference between AdBDNF and AdNull-treated olfactory bulb BrdU labeling indices was significant to p<0.001. No other comparisons based on total BrdU+ cell counts were significant. However, whereas BrdU+ cell addition to non-olfactory regions was almost entirely non-neuronal in AdNull control rats, the BrdU+ cell population included newly generated neurons in several regions of the AdBDNF-injected brains. Thus, when BrdU+/β-III-tubulin+ neurons were specifically compared between AdBDNF and AdNull-treatment groups, a significant effect of AdBDNF on neuronal recruitment to the striatum was noted (see below). Abbreviations: VZ, ventricular zone; RMS, rostral migratory stream; OB, olfactory bulb; Sep, septum; Str, neostriatum; Ctx, neocortex.

Despite the extraordinary increase in olfactory neuronal recruitment in AdBDNF-treated rats, this treatment was not associated with significantly increased cell division outside of the olfactory system. As shown in FIG. 7, the mean numbers of BrdU+ cells per section in the frontal cortex, septum, and striatum were all roughly equivalent in the AdBDNF- and AdNull-injected brains, when assessed 20 days after viral injection. Nonetheless, this left open the possibility that AdBDNF might be influencing either the lineage choice of mitotically-active progenitors, or the selective survival of their neuronal daughters. To assess this possibility, the incidence of β-III-tubulin+/BrdU+ cells in each non-olfactory region studied were scored, in both AdBDNF and AdNull treated brains. When BrdU+ cells were identified by epifluorescence microscopy, they were subjected to two color confocal imaging with serial sections in the z plane, to estimate the incidence of double-labeled β-III-tubulin+/BrdU+ cells, while ensuring that the BrdU+ nuclei indeed belonged to β-III-tubulin+ cell profiles.

Figure 8A:
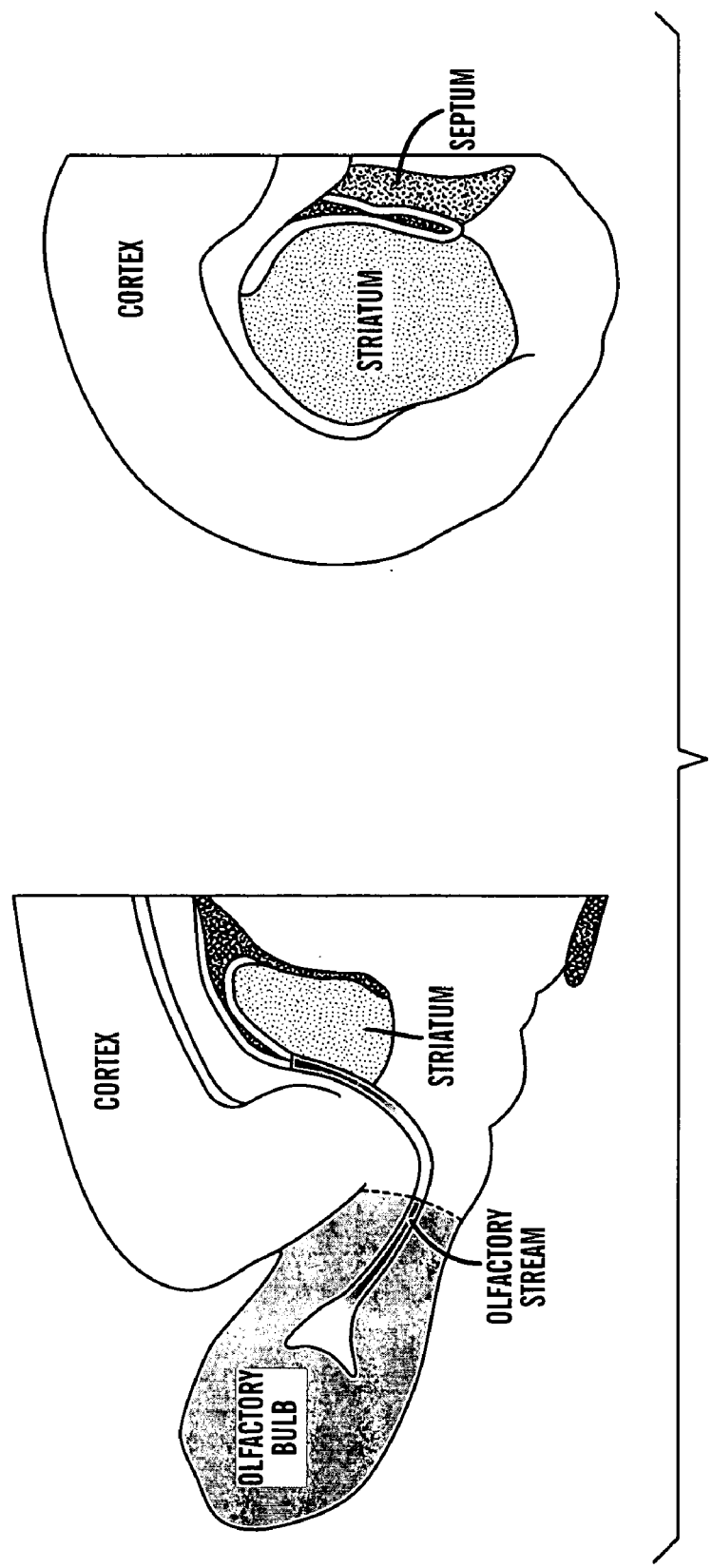
FIGS. 8A–B show AdBDNF treatment was associated with neuronal addition to the neostriatum.

Only very rare BrdU+/β-III-tubulin+ neurons were found in the frontal cortex of AdBDNF-treated animals, too few to merit systematic comparison to null controls. No examples of newly generated septal neurons were found in either the AdBDNF or AdNull-injected animals. Surprisingly the AdBDNF treated animals were found to harbor a distinct population of newly generated neurons in the neostriatum, as shown in FIG. 8 and FIG. 9. These BrdU+ neurons comprised a distinct minority of the BrdU+ striatal cells in these brains. They were scattered throughout the striatum, though they were most often located in its periventricular third. Confocal imaging confirmed examples of newly generated, BrdU+ striatal cells that expressed a variety of independent markers of neuronal phenotype, that included β-III tubulin, NeuN, GAD67, DARRP-32, and calbindin-D28K. FIG. 9 shows the AdBDNF induced heterotopic addition of BrdU+/β-III-tubulin+ neurons to the striatum. FIG. 10 shows the expression of neuronal markers of NeuN, GAD67, DARRP-32, and calbindin-D28K in the newly recruited striatal neurons. FIG. 11 shows that expression markers of BrdU+/β-III-tubulin+, BrdU+/GAD67, and BrdU+/DARRP-32 persist 5–8 weeks after AdBDNF injection.

Figure 8B:
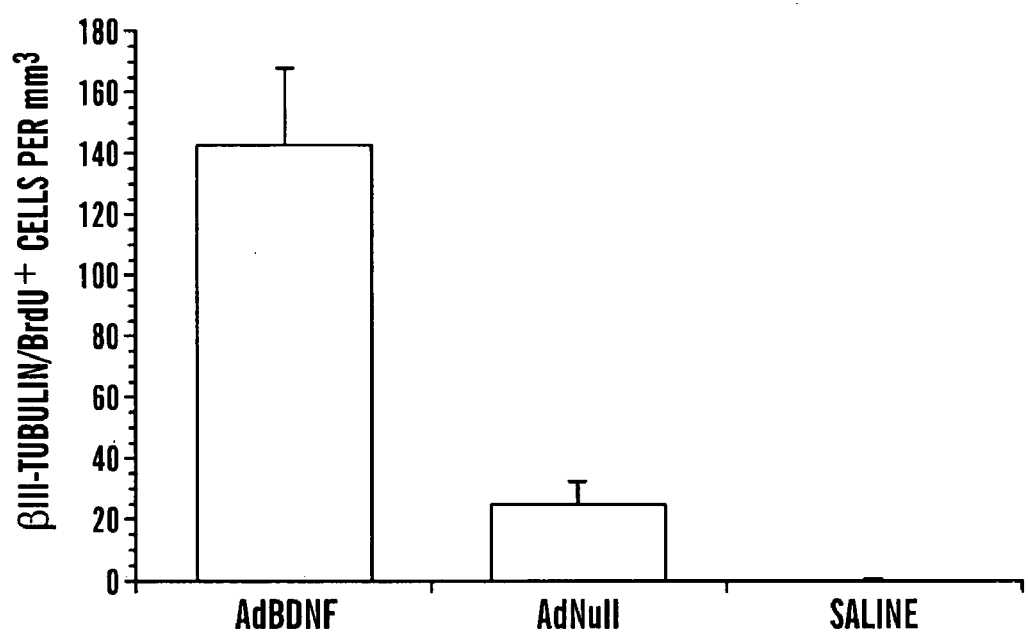
Figure 9C:
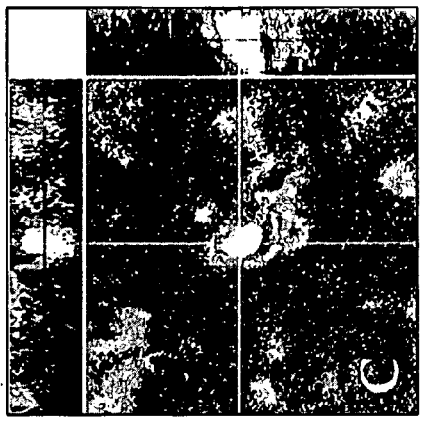
FIGS. 9A–L are confocal images of BrdU-labeled neurons found in the neostriata of AdBDNF-treated rats, 3 weeks after virus injection, demonstrating the induced the heterotopic addition of BrdU+/β-III-tubulin+ neurons to the striatum. These cells were identified by immunostaining for both BrdU and β-III-tubulin.
Figure 9B:
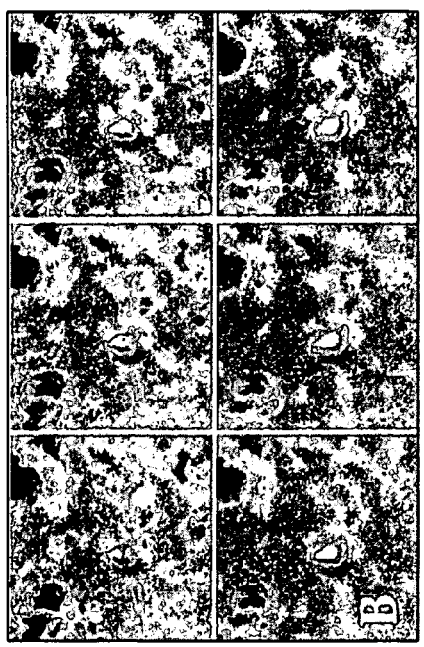
Figure 9A:
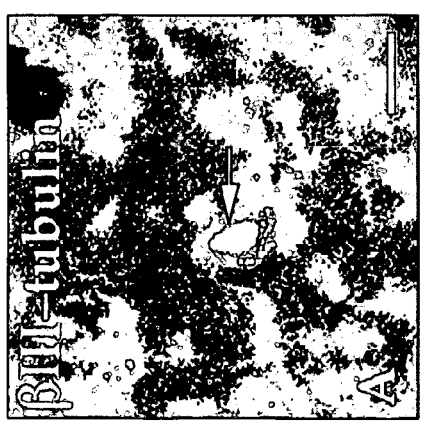
Figure 9F:
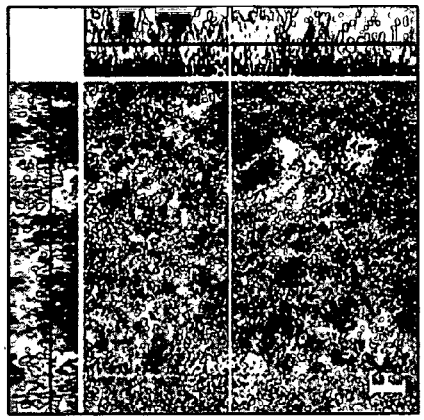
Figure 9E:
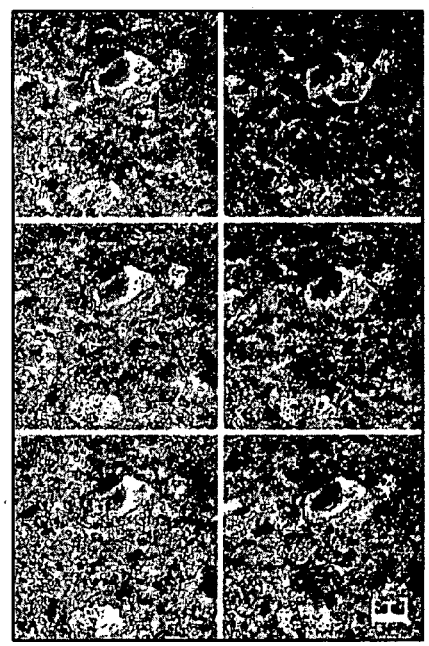
Figure 9D:
Figure 9I:
Figure 9H:
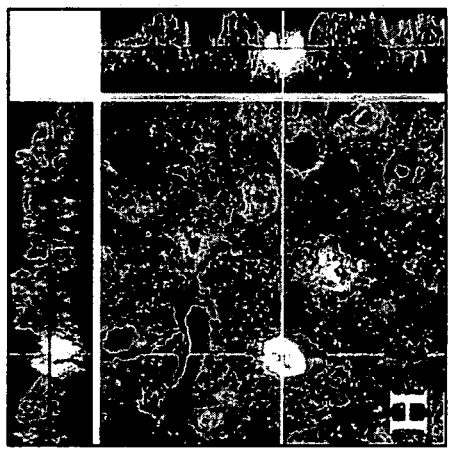
Figure 9G:
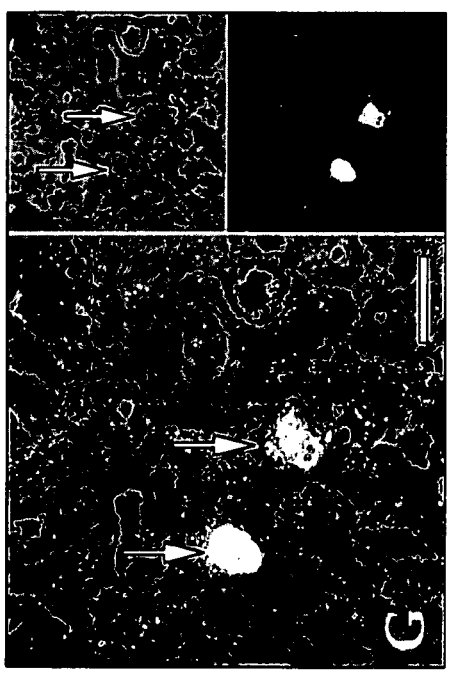
Figure 9J:
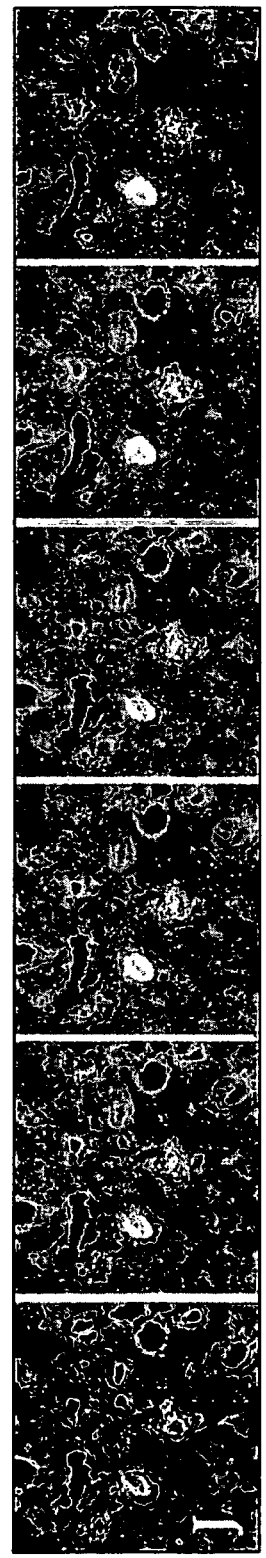
Figure 9K:
Figure 9L:
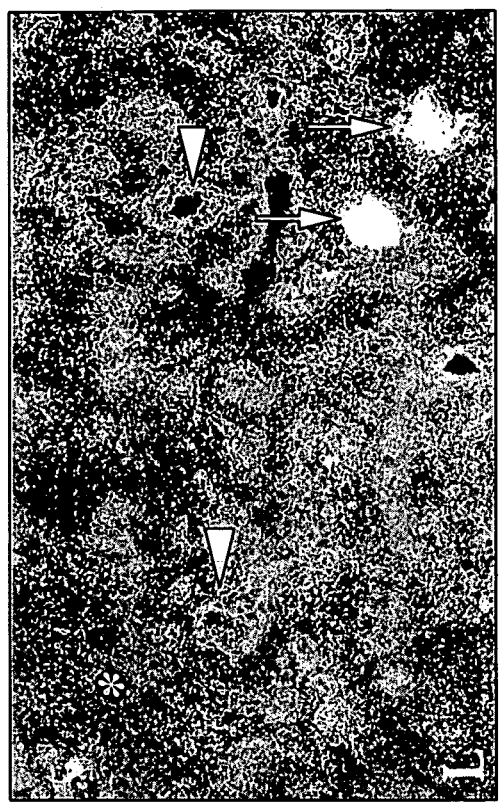
Figure 10A:
FIGS. 10A–I show newly recruited striatal neurons include medium spiny neurons. The BrdU+ neurons found in AdBDNF-treated striata expressed neuronal markers other than β-III-tubulin, which included NeuN. They also expressed characteristic antigenic markers of medium spiny neurons of the adult caudate-putamen, including calbindin-D28k, glutamic acid decarboxylase (GAD67), and DARPP-32.
Figure 10B:
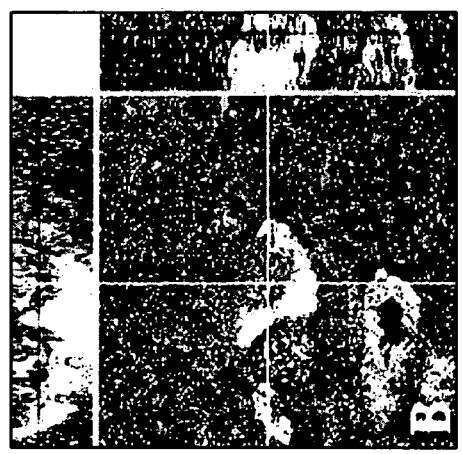
Figure 10C:
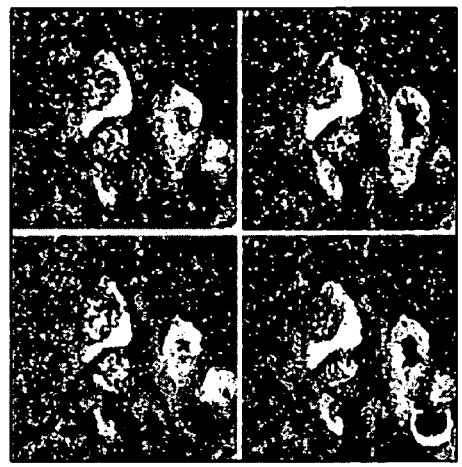
Figure 10F:
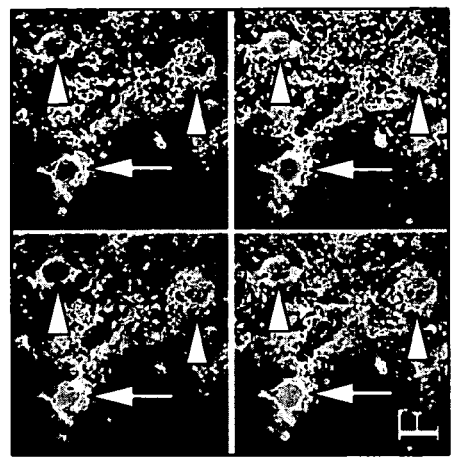
Figure 10E:
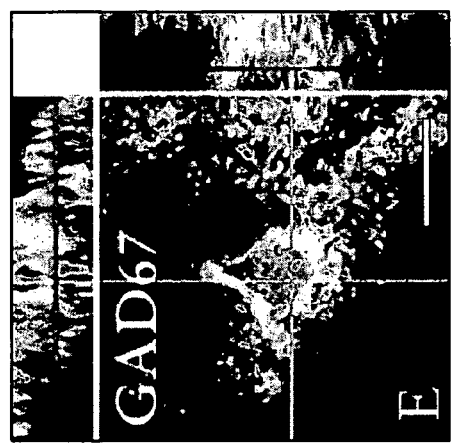
Figure 10D:
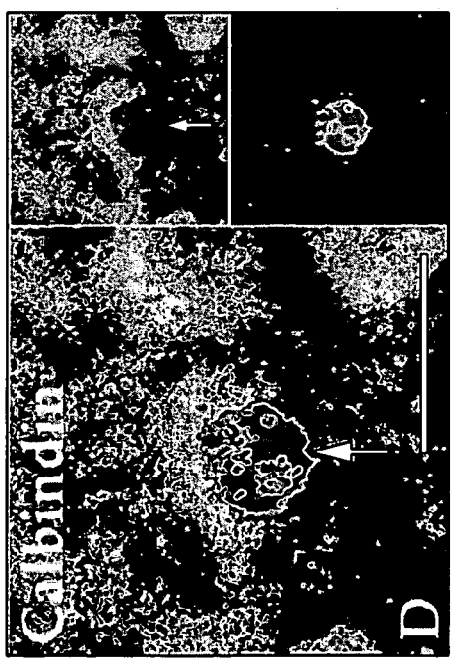
Figure 10I:
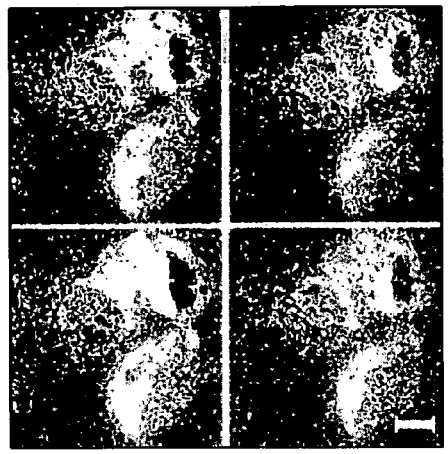
Figure 10H:
Figure 10G:
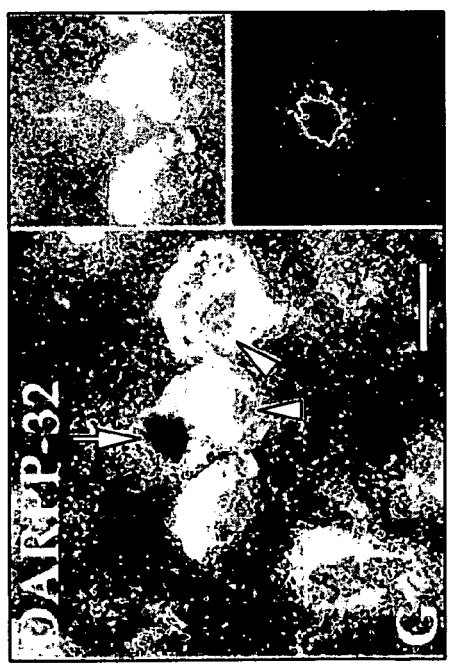
Figure 11C:
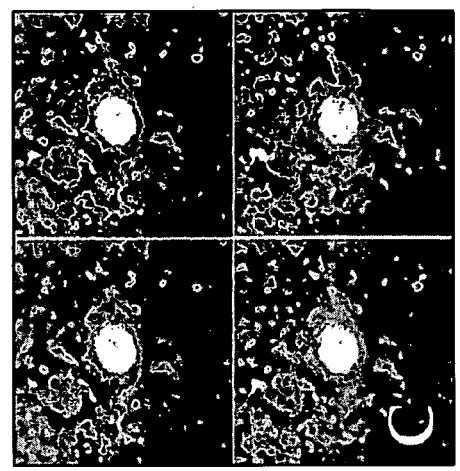
FIGS. 11A–C show a typical β-III-tubulin+/BrdU+ neuron found in an AdBDNF-treated striatum, 8 weeks after virus injection.
Figure 11B:
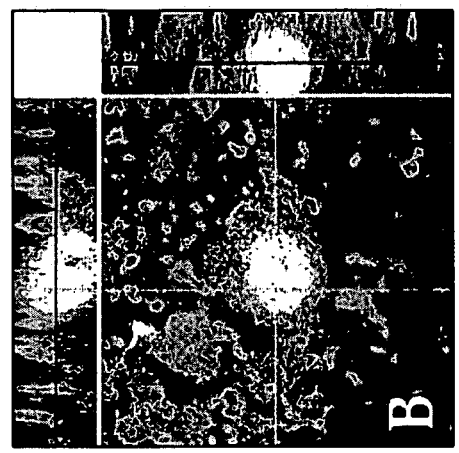
Figure 11A:
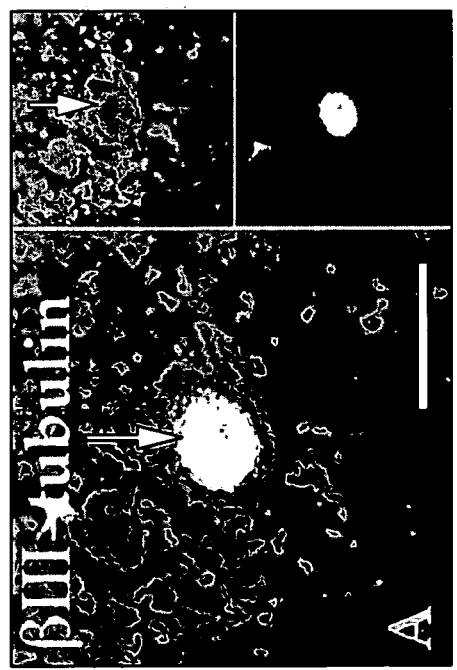
Figure 11F:
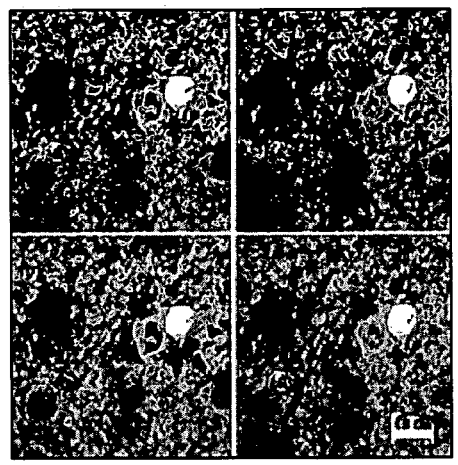
FIGS. 11D–F are analogous images of a GAD67+/BrdU+ neuron, viewed in an AdBDNF-treated striatum at 8 weeks. Only one of the two adjacent GAD67+ neurons (arrow) is BrdU-labeled.
Figure 11E:
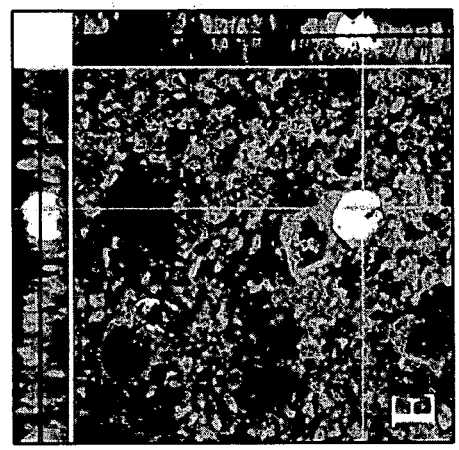
Figure 11D:
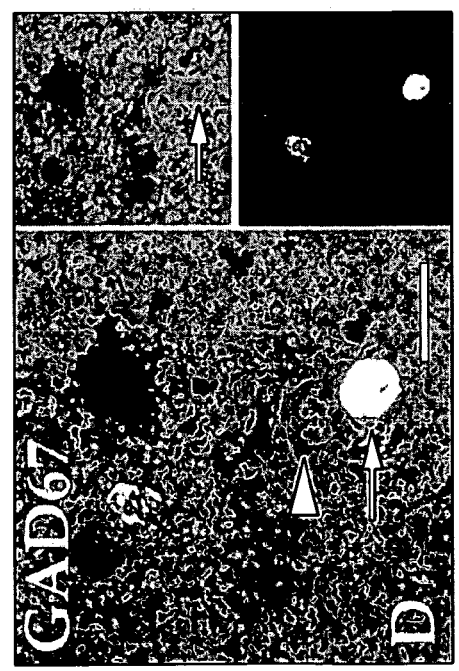
Figure 11I:
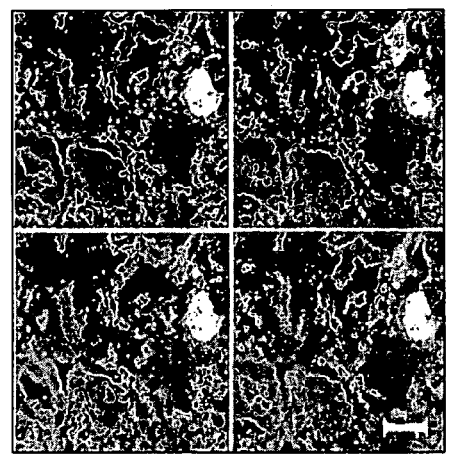
FIGS. 11G–I show a representative DARPP-32+/BrdU+ neuron, again found in an AdBDNF-treated striatum 8 weeks after virus injection.
Figure 11H:
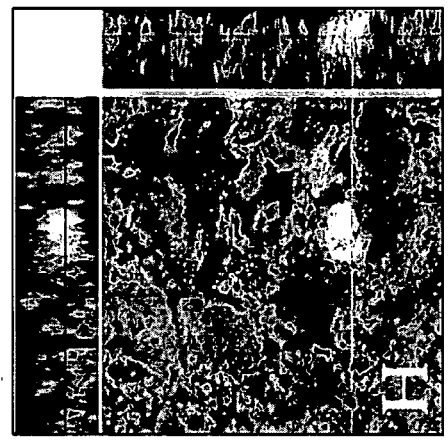
Figure 11G:

Quantitatively, unbiased counting of all striatal BrdU+ cells in sagittal sections of AdBDNF-treated animals revealed an average of 1663±748 BrdU+ cells/mm$^3$. Among a randomly chosen sample of 477 BrdU+ striatal cells located in sections (n=17) selected from 3 AdBDNF-treated brains, 41 cells (8.3±2.3%) could be confirmed as double-labeled for both BrdU and β-III-tubulin by confocal imaging, as shown in FIG. 9. This compared to the complete absence of double-labeled striatal neurons in the PBS-injected rats (0/95 cells, n=8 sections taken from 3 rats), and to the relatively rare incidence of BrdU+/β-III-tubulin+ neurons observed in the AdNull-injected rats—15 among 591 randomly chosen BrdU+ striatal cells (2.1±1.1%; n=23 sections taken from 6 rats, shown in FIG. 8B. Analysis of variance (ANOVA) established that the incidence of new striatal neurons in the AdBDNF-injected rats and their controls differed significantly (p=0.006; F=9.48 [2, 9 d.f.]). On a per animal basis, 8.3±2.3% of the BrdU+ cells in the AdBDNF-treated rat striata, or 143±26.5 cells/mm$^3$, were antigenically-definable as neurons, as shown in FIG. 8B. This represented only 0.34% (=143/41,637) of the total striatal neuronal pool. However, since these cells were generated in just 3 weeks, one might predict that proportionately more neurons may be added to the striatum with longer survival times (see below), provided that both viral BDNF expression and progenitor cell competence are sustained.

Example 16

No Neurogenesis Noted in Untreated Adult Striatum

To assess the incidence, if any, of neuronal addition to the normal untreated neostriatum, control animals that were injected intraventricularly with either PBS (n=3) or AdNull (n=5), who received BrdU on days 2 through 19, and which were then sacrificed on the next day (3 wk time point) were examined. In the PBS-injected rats, no BrdU+/β-III-tubulin+ striatal neurons were found, as shown in FIG. 8B. In these same rats, constitutive neurogenesis was observed in both the olfactory bulb and dentate gyrus, as would be expected, though no attempt was made at quantifying baseline neuronal recruitment at these sites. Thus, no evidence was found of constitutive neurogenesis in the normal unstimulated neostriatum, in contrast to the robust neuronal recruitment observed in the AdBDNF-treated striatum.

Example 17

Adenoviral Infection per se Associated with a Minor Induction of Neuronal Recruitment Interestingly, and in contrast to the absence of striatal neuronal addition noted in the PBS-treated rats, the AdNull-injected controls did exhibit a small amount of constitutive neuronal addition to the striatum. As noted above, among 591 BrdU+ striatal cells identified in AdNull-injected rats sacrificed at 3 weeks, confocal analysis revealed that 15 cells (2.1±1.1%) double-labeled for BrdU and β-III-tubulin. This was determined using the same criteria as in the concurrent analysis of AdBDNF-treated striata, and the cells were assessed by the same individuals, who were blinded as to treatment group. As noted above, and shown in FIG. 8B, this incidence of striatal neuronal addition in the AdNull-treated rats was significantly less (p=0.006) than the 8.3±2.2% noted in their AdBDNF-treated counterparts. Nonetheless, the very presence of BrdU+/β-III-tubulin+ neurons in the AdNull-treated striata was surprising, given the absence of any new striatal neurons in the PBS-injected rats, and suggested that adenoviral infection itself might have resulted in some mobilization of neural progenitors. This raised the possibility that virally-induced ependymal cytokines may influence subependymal neuronal production or migration; this in turn might allow otherwise heterotopic neuronal recruitment. Nonetheless, the substantial increase in striatal neuronal addition in the AdBDNF-treated rats, relative to their AdNull-treated controls, suggested that any adenovirus-associated mobilization of neural progenitor cells was minor relative to that specifically attributable to BDNF. Together, these observations indicated that AdBDNF induced the addition of new neurons to the neostriatum, an otherwise atypical site for neuronal recruitment in the adult brain.

Example 18

AdBDNF-Induced Striatal Neurons Expressed Antigens of Medium Spiny Neurons

To assess the neuronal phenotype induced by AdBDNF infection, sections of AdBDNF-treated brains were immunostained for a number of markers of striatal phenotype. As shown in FIG. 10, some BrdU+ striatal cells expressed calbindin-D28K, a marker of medium spiny neurons of the caudate-putamen (Burke, R. et al., "Relative Loss of the Striatal Striosome Compartment, Defined by Calbindin-D28 Immunostaining, Following Developmental Hypoxic-Ischemic Injury," Neuroscience 56:305–315 (1993); Waldvogel, H. et al, "Differential Sensitivity of Calbindin and Parvalbumin Immunoreactive Cells in the Striatum to Excitotoxins," Brain Res. 546:329–335 (1991), which are hereby incorporated by reference in their entirety). Similarly, also shown in FIG. 10, abundance of BrdU+ striatal cells that co-expressed glutamic acid decarboxylase (GAD67), a characteristic marker for GABAergic neurons, were identified.

Despite their expression by medium spiny neurons, both calbindin and GAD67 are expressed by other cell types, and even within the striatum may not be definitive markers of medium spiny neurons. Thus, to better ascertain the phenotype of AdBDNF-induced striatal neurons, double-staining for DARPP-32 (dopamine and cAMP-regulated phosphoprotein, of 32 kDa), a highly selective marker of medium spiny neurons (Ivkovic, S. et al, "Expression of the Striatal DARPP-32/ARPP-21 Phenotype in GABAergic Neurons Requires Neurotrophins in Vivo and In Vitro," J. Neurosci 19:5409–5419 (1999), which is hereby incorporated by reference in its entirety), was carried out on sections derived from the same animals that expressed calbindin and GAD67. Among the rats sacrificed 3 weeks after virus injection, 6 of a random sample of 125 BrdU+ striatal cells (4.8%) were found to be DARPP-32+, and were confirmed as such by confocal imaging and serial reconstruction, as shown in FIG. 10. This compared to 33 of 377 BrdU+ cells (8.8%) in adjacent sections of the same rats that expressed β-III-tubulin. Importantly, the percentage of DARPP-32+ cells among the BrdU+ striatal cell population increased with time, such that when assessed in rats sacrificed 8 weeks after AdBDNF injection, 10 of 128 BrdU+ cells (7.8%) were DARPP-32+ (see below). Together, these observations suggested that many, if not most, of the AdBDNF-induced striatal cells matured to a phenotype characteristic of medium spiny neurons. These data raise the possibility that AdBDNF treatment might contribute to the restoration of this phenotype, a critical mediator of striatopallidal communication, whose significance is underscored by its selective loss in Huntington's Disease.

Example 19

AdBDNF-Induced Striatal Neurons Matured and Survived

The 3 week time point used to establish neuronal recruitment in response to AdBDNF allowed the possibility that those cells generated and detected at 3 weeks were merely transitional phenotypes, perhaps transient in their very existence. To establish the more prolonged survival of AdBDNF-associated striatal neurons, a distinct group of animals that were sacrificed and assessed 8 weeks after viral injection. Both β-III-tubulin+/BrdU+ and DARPP32+/BrdU+ double-labeled striatal cells persisted in these rats, with little apparent loss, as shown in FIG. 11. Among a sample of 106 BrdU+ cells in 3 8-week rat striata randomly sampled for confocal imaging, 7 cells (6.6%) were found to express β-III-tubulin. Similarly, 10 of 128 sampled BrdU+ cells (7.8%) expressed DARPP-32. The rough equivalency of the proportion of BrdU+ striatal cells that were β-III-tubulin+ and DARPP+ argued that by 8 weeks after AdBDNF injection, or 5 weeks after the last BrdU incorporation, virtually all of the BrdU+ neurons, as defined by β-III-tubulin, also would have been expected to express DARPP-32. Thus, a substantial number of AdBDNF-induced striatal neurons survived, depending upon the time point of their generation during the BrdU injection course, for at least 5–8 weeks after terminal mitosis. Furthermore, these surviving neurons matured sufficiently to express DARPP-32, a relatively mature marker of striatal neuronal phenotype. As such, these AdBDNF-induced neurons did not appear to constitute transitional phenotypes.

Example 20

AdBDNF Treatment Associated with Systemic Weight Loss

The AdBDNF-injected animals were noted to experience a stereotypic weight loss during the 3 week period between AdBDNF delivery and sacrifice. This was not unexpected, since weight loss has previously been described in rats receiving intraventricular BDNF infusions. This syndrome appears to be central in origin, and reflects BDNF-associated appetite suppression and hypophagia, rather than any hypermetabolic state (Pelleymounter, M. et al, "Characteristics of BDNF-induced Weight Loss," Exp. Neurol. 131:229–238 (1995), which is hereby incorporated by reference in its entirety). It was found that this was not an effect of the virus, in that neither AdNull nor PBS-injected animals experienced similar weight loss. Whereas AdNull-injected controls rose from 300±16 g at the time of viral injection, to 339±6 g at the time of sacrifice 3 weeks later (n=4), a matched set of AdBDNF-treated animals lost weight during that period, falling from 328±34 to 288±17 g/animal (p=0.016 by ANOVA, comparing the slopes of weight gain as a function of time between AdBDNF, AdNull and PBS-treated rats [F=6.17; 2, 13 d.f.])

The time course of weight loss in the AdBDNF-treated animals suggested that virally-delivered BDNF was exerting rapid and powerful biological effects on the target nervous system, within the same time frame as the BDNF-associated rise in neuronal recruitment. Whether this anorexic phenotype was a consequence of olfactory neuronal addition and altered olfactory perception, or was instead an unrelated effect of central BDNF overexpression, remains to be established.

Infection of the adult rat ventricular lining with an adenoviral BDNF expression vector is shown herein to induce the recruitment of new neurons from resident progenitor cells of the forebrain ventricular zone. In particular, adenoviral infection resulted in the diffuse transduction of the adult ventricular wall, with the effective subrogation of the ependyma into a source of secreted BDNF to both the CSF and periventricular parenchyma. This resulted in the sustained, high-level secretion of BDNF by the ventricular wall, and was associated with a >2.4-fold increase in the recruitment of new neurons to the rat olfactory bulb over the 3 weeks following viral administration. Importantly, AdBDNF administration was also associated with the heterotopic addition of new neurons to the neostriatum, with the recruitment of BrdU-incorporating β-III-tubulin+/DARPP-32+/NeuN+/GAD67+/calbindin-D28K+ neurons to the striata of AdBDNF-treated animals. These experiments comprise the first use of viral gene delivery as a means to induce neurogenesis from resident progenitor cells in the adult CNS. In addition, they present the first evidence for induced neuronal addition to the mature neostriatum. Thus, the present invention indicates that viral transduction of the adult ependyma to overexpress BDNF may be an effective means of inducing the recruitment of new neurons to permissive regions of the mature brain.

Predominantly ependymal cell expression of both BDNF and GFP mRNAs were observed after intraventricular injection of AdBDNF:IRES:GFP. Nonetheless, occasional subependymal labeling was noted, particularly along the subcallosal and dorsolateral walls of the lateral ventricles. When present, subependymal GFP fluorescence appeared as rapidly as ependymal cell labeling; both were evident by 7 days after virus injection, as shown in FIG. 1. GFP+ cells were limited to the ventricular layers, though, and were never noted in either the olfactory subependyma or striatal parenchyma, except for migrants into the corpus callosum. Despite this restriction of virally-expressed BDNF to the ventricular wall, newly generated neurons, derived from uninfected subependymal cells, were profoundly influenced in their production and survival by their genesis adjacent to AdBDNF-infected ependymal cells. Thus, the effects of ependymal BDNF on neurogenesis and neuronal recruitment to the olfactory bulb likely derived from a paracrine effect of ependymal BDNF upon uninfected subependymal progenitors. Furthermore, BDNF's effects were presumably exerted early in the ontogeny of these cells, before their departure from the ventricular wall, since it is unclear whether ependymal secretion of BDNF to the CSF and periventricular parenchyma would have influenced BDNF in the olfactory bulb itself. Indeed, the mature olfactory bulb harbors high levels of BDNF, while the neurotrophin appears relatively sequestered from the adult ventricular zone and olfactory subependyma. Thus, a likely scenario is that ependymal BDNF acts to promote the early differentiation and survival during migration of newly generated, subependymally-derived neurons, and that these cells survive to migrate into an already BDNF-rich environment in the olfactory bulb. As such, neuronal mitogenesis and departure from the ventricular wall may be viewed as the initial rate-limiting steps for neuronal recruitment, with the cells finding a permissive environment for survival once in the bulb.

Importantly, AdBDNF injection was also associated with the addition of new neurons to the neostriata of treated animals. Such neuronal addition to non-granule cell populations has only rarely been reported in the adult mammalian brain, specifically in the visual cortex (Kaplan, M., "Proliferation of SubepenDymal Cells in the Adult Primate CNS: Differential Uptake of Thymidine by DNA-Labeled Precursors," *J. Hirnforsch* 23:23–33 (1983), which is hereby incorporated by reference in its entirety) and macaque frontal cortex (Gould, E. et al., "Neurogenesis in the Neocortex of Adult Primates," *Science* 286:548–552 (1999), which is hereby incorporated by reference in its entirety), as well as in response to injury in the adult mouse frontal cortex (Magavi, S. et al, "Induction of Neurogenesis in the Neocortex of Adult Mice," *Nature* 405:951–955 (2000), which is hereby incorporated by reference in its entirety). More generally though, reports of neurogenesis in the adult mammalian brain have been limited to olfactory, hippocampal, and cerebellar granule cell populations (reviewed in Goldman, S. A. et al., "Strategies Utilized by Migrating Neurons of the Postnatal Vertebrate Forebrain," *Trends in Neurosciences* 21:107–114 (1998), which is hereby incorporated by reference in its entirety). Nonetheless, careful analysis of serially-reconstructed confocal images revealed that AdBDNF-injected animals harbored a discrete cohort of antigenically confirmed neurons that co-labeled with BrdU and were scattered throughout the neostriatum. Since the adult neostriatum typically does not add new neurons, the induced neuronal addition associated with AdBDNF treatment may be viewed as heterotopic in nature.

Even though their numbers were small relative to the much larger pool of AdBDNF-induced olfactory neurons, the recruitment kinetics of the induced striatal pool were surprisingly robust. Given an average striatal neuronal BrdU labeling index of 0.34%, and an average of $1.03 \times 10^6 \pm 6.56 \times 10^4$ neurons per striatum, roughly $3.5 \times 10^3$ neurons may be added to each striatum over an 18 day period of BrdU injection, or approximately 195 neurons/striatum/day. This estimate is crude and likely an underestimate in that it is predicated on the assumptions that daily BrdU injections label the entire mitotic pool and that no striatal cells are dying during this period. In addition, these numbers may reflect but one point on the dose-response curve relating neuronal recruitment to BDNF expression levels. It is important to remember that in the above examples neither the dose of adenovirus, nor that of its expressed BDNF were perturbed. Nonetheless, these numbers suggest that AdBDNF-induced neuronal addition may be sufficiently robust to contribute meaningfully to striatal function, if not architecture. Furthermore, the identification of many AdBDNF-induced neurons as DARPP-32+/GAD67+/calbindin-D28K+ suggests that at least a significant fraction of these neurons may be homologous to the medium spiny interneuron population of the adult neostriatum. Since this is the neuronal population lost in Huntington's Disease and the striatonigral degenerations, transduction of the ventricular wall with BDNF expression vectors might be envisaged as a feasible strategy for restoring diminished neuronal populations in the striatal degenerations, as well as in other conditions of acquired striatal neuronal loss.

Interestingly, it was noted that the AdNull (AdCMV: hGFP)-injected controls exhibited a small amount of constitutive neuronal addition to the striatum. This did not appear to reflect neurogenesis in the normal striatum, since PBS-injected rats exhibited no striatal neuronal addition whatsoever. Rather, these results suggested that adenoviral infection per se might have been sufficient to instigate mobilization of neural progenitors. Although minor in extent and significantly less robust than AdBDNF-induced neuronal recruitment, the AdNull induction of striatal neuronal addition may represent a hitherto unrecognized feature of central viral infection, especially of the ependyma/subependyma. Presumably, virally-induced ependymal cytokines might stimulate subependymal neurogenesis, and thereby permit otherwise heterotopic neuronal recruitment. This possibility is strengthened by reports that adenovirally-induced cytokines include IL-6 and IL-8, both of which have been found to be neurotrophic in vitro (Driesse, M. et al, "Intra-CSF Administered Recombinant Adenovirus Causes an Immune Response-Mediated Toxicity," *Gene Therapy* 7:1401–1409 (2000), which is hereby incorporated by reference in its entirety). Indeed, such paracrine activation of neurotrophic cytokines might explain recent observations of both inflammation and apoptosis-related neuronal recruitment in the adult brain (Magavi, S. et al, "Induction of Neurogenesis in the Neocortex of Adult Mice," *Nature* 405:951–955 (2000); Wang, Y. et al, "Cortical Interneurons Upregulate Neurotrophins In Vivo in Response to Targeted Apoptotic Degeneration of Neighboring Pyramidal Neurons," *Exp. Neurol.* 154:389–402 (1998), which are hereby incorporated by reference in their entirety). In any event, the significant increase in neuronal recruitment to the striatum in the AdBDNF-treated rats, relative to their AdNull-treated controls, argued that any virus-associated cell genesis paled beside that specifically associated with BDNF.

It is worth noting that despite the frequent observation of BrdU-incorporating cells in the septa, striata, and frontal cortices of these animals, no significant differences were noted between the AdBDNF and control animals in their BrdU-labeled cell numbers, as shown in FIG. 7. As shown in FIGS. 8 and 9, AdBDNF treatment was associated with an increase in the relative proportion of neurons among the BrdU+ cells of the neostriatum. Nonetheless, the percentage of confocal-validated new neurons in the overall striatal BrdU+ cell population was so small—just 8% of the BrdU+ population—that AdBDNF would not have been expected to yield readily demonstrable treatment-related differences in either the total BrdU+ cell number or overall striatal neuronal number. The induction of striatal neurogenesis by AdBDNF might therefore reflect either the neuronal differentiation of postmitotic daughters that might otherwise have become glia, or the postmitotic rescue of daughters otherwise destined to die. Indeed, although a number of studies have failed to observe any mitogenic effect of BDNF on ventricular zone progenitor cells (Ahmed et al.,. "BDNF Enhances the Differentiation but not the Survival of CNS Stem Cell-Derived Neuronal Precursors," *J Neurosci.* 15:5765–78 (1995); Kirschenbaum, B. et al, "Brain-derived Neurotrophic Factor Promotes the Survival of Neurons Arising from the Adult Rat Forebrain Subependymal Zone," *Proc Nat'l Acad Sci USA* 92:210–4 (1995), which are hereby incorporated by reference in their entirety), these data do not allow one to rule out a direct mitogenic effect in vivo.

It is important to also consider the possibility that BDNF might act not only to recruit a ventricular zone-derived population, but also to activate resident parenchymal glial progenitors to differentiate as neurons. Studies of both adult rat (Palmer, T. et al, "FGF2 Activates a Latent Neurogenic Program in Neural Stem Cells from Diverse Regions of the Adult CNS," *J. Neurosci.* 19:8487–8497 (1999), which is hereby incorporated by reference in its entirety) and human (Roy, N. et al, "Identification, Isolation and Enrichment of Oligodendrocyte Progenitor Cells from the Adult Human Subcortical White Matter," *J. Neurosci.* 19:9986–9995 (1999), which is hereby incorporated by reference in its entirety) brain have indicated the ability of white matter progenitor cells to differentiate as neurons in vitro. In the AdBDNF-treated neostriata in particular, the possibility of AdBDNF-induced neurogenesis from parenchymal progenitors is suggested by the frequent observation of clustered pairs of BrdU+ neurons (e.g., FIG. 9G), although continued division of ventricular zone migrants might also explain this observation (Menezes, J. R. et al, "The Division of Neuronal Progenitor Cells During Migration in the Neonatal Mammalian Forebrain," *Mol Cell Neurosci* 6:496–508 (1995), which is hereby incorporated by reference in its entirety). Thus, while the possibility that AdBDNF might stimulate neuronal recruitment from parenchymal progenitors is intriguing, the above data do not yet allow the source or migration routes of AdBDNF-induced striatal neurons to be addressed.

The implications of AdBDNF-induced striatal neurogenesis may be profound, particularly for disorders such as Huntington's Disease and striatonigral degeneration, in which the loss of striatal neurons may dictate the pathology. The apparent assumption of a medium spiny neuronal phenotype by many, and perhaps most, AdBDNF-induced neostriatal neurons is especially intriguing, in that it suggests the potential therapeutic utility of this neuronal population. Axiomatically, if these cells prove functional and able to survive, then AdBDNF-induced striatal neurons might be able to delay, abrogate, or reverse striatal neurodegenerative disease. Nonetheless, it remains to be seen whether these AdBDNF-induced neurons can functionally integrate, both with resident striatal neurons and nigrostriatal afferents, whether they can survive longer than 5–8 weeks, and whether they can survive the primary disease process better than the cells they are intended to replace. These uncertainties notwithstanding, the adenoviral BDNF-mediated induction of neuronal addition to the adult brain expands the current conception of cellular plasticity in the adult CNS, while lending a new perspective to the potential for gene therapy in the treatment of structural neurological condition.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A method of inducing addition of medium spiny neurons in post-natal and adult brain comprising:
   providing a nucleic acid construct encoding a brain-derived neurotrophic factor and a nucleic acid construct encoding noggin, wherein the nucleic acid constructs are in viral vectors, and
   injecting said viral vectors into a subject's lateral ventricles to infect the ventricular wall under conditions effective to express the neurotrophic factor and noggin and to induce addition of medium spiny neurons in any one or all of the caudate nucleus and the putamen of the subject.

2. The method according to claim 1, wherein the viral vectors are selected from the group consisting of an adenoviral vector, a lentiviral vector, a retroviral vector, an adeno-associated viral vector, and a combination thereof.

3. The method according to claim 1, wherein the nucleic acid construct encoding the brain-derived neurotrophic factor further comprises a constitutive promoter for controlling expression of the brain-derived neurotrophic factor.

4. The method according to claim 1, wherein the nucleic acid construct encoding the brain-derived neurotrophic factor further comprises a cell-specific promoter for controlling expression of the brain-derived neurotrophic factor.

5. The method according to claim 1, wherein the nucleic acid construct encoding the brain-derived neurotrophic factor further comprises an inducible or conditional promoter for controlling expression of the brain-derived neurotrophic factor.

6. A method of inducing addition of medium spiny neurons in a subject having Huntington's disease comprising:
providing a nucleic acid construct encoding a brain-derived neurotrophic factor and a nucleic acid construct encoding noggin, wherein the nucleic acid constructs are in viral vectors, and
injecting said viral vectors into the subject's lateral ventricles to infect the ventricular wall under conditions effective to express the neurotrophic factor and noggin and to induce addition of medium spiny neurons in any one or all of the caudate nucleus and the putamen of the subject.

7. The method according to claim 6, wherein the viral vectors are selected from the group consisting of an adenoviral vector, a lentiviral vector, a retroviral vector, an adeno-associated viral vector, and a combination thereof.

8. The method according to claim 6, wherein the nucleic acid construct encoding the brain-derived neurotrophic factor further comprises a constitutive promoter for controlling expression of the brain-derived neurotrophic factor.

9. The method according to claim 6, wherein the nucleic acid construct encoding the brain-derived neurotrophic factor further comprises a cell-specific promoter for controlling expression of the brain-derived neurotrophic factor.

10. The method according to claim 6, wherein the nucleic acid construct encoding the brain-derived neurotrophic factor further comprises an inducible or conditional promoter for controlling expression of the brain-derived neurotrophic factor.

* * * * *